(12) United States Patent
Zoller et al.

(10) Patent No.: US 8,735,437 B2
(45) Date of Patent: May 27, 2014

(54) IMIDAZOLIDINE CARBOXAMIDE DERIVATIVES AS LIPASE AND PHOSPHOLIPASE INHIBITORS

(75) Inventors: Gerhard Zoller, Schöneck (DE); Stefan Petry, Frankfurt am Main (DE); Gunter Müller, Frankfurt am Main (DE); Norbert Tennagels, Frankfurt am Main (DE)

(73) Assignee: Sanofi, Paris (FR)

( * ) Notice: Subject to any disclaimer, the term of this patent is extended or adjusted under 35 U.S.C. 154(b) by 908 days.

(21) Appl. No.: 12/572,462

(22) Filed: Oct. 2, 2009

(65) Prior Publication Data

US 2010/0105719 A1      Apr. 29, 2010

Related U.S. Application Data

(63) Continuation of application No. PCT/EP2008/002231, filed on Mar. 20, 2008.

(30) Foreign Application Priority Data

Apr. 5, 2007   (EP) .................................. 07007161

(51) Int. Cl.
*A01N 43/50*  (2006.01)
*A61K 31/415* (2006.01)

(52) U.S. Cl.
USPC .......................................... 514/385; 514/396

(58) Field of Classification Search
USPC ........................ 514/359, 385, 396
See application file for complete search history.

(56) References Cited

U.S. PATENT DOCUMENTS

2002/0032196 A1* 3/2002 Haddach et al. ............ 514/229.8

FOREIGN PATENT DOCUMENTS

| JP | 03227976 | 10/1991 |
|---|---|---|
| JP | 11147878 | 6/1999 |
| WO | WO 2004/093872 | 11/2004 |
| WO | WO 2004/094393 | 11/2004 |
| WO | WO 2004/094394 | 11/2004 |
| WO | WO 2005/087236 A1 * | 9/2005 |
| WO | WO 2006/111321 | 10/2006 |

OTHER PUBLICATIONS

Shen et al. ("Transition-metal-catalyzed reactions of 5-methylene-2-oxazolidinone and 5-methylene-1,3-thiazolidine-2-thione with isocyanates" Appl. Organometal. Chem. 2003, 17, 767-775).*
Lewis, R. T., et. al., Tryptophan-Derived NK1 Antagonists: Conformationally Constrained Heterocyclic Bioisosteres of the Ester Linkage, J. Med. Chem., (1995), vol. 38, pp. 923-933.
Pirkle, W. H., et. al., Preparation of a-Substituted a-Amino Acids of High Enantiomeric Purity, Chirality, vol. 4, pp. 302-307. (1992).
Boeijen, A., et. al., Combinational Chemistry of Hydantoins, Bioorganic & Medicinal Chemistry Letters, vol. 8, (1998), pp. 2375-2380.

* cited by examiner

*Primary Examiner* — Yong Chong
(74) *Attorney, Agent, or Firm* — Scully, Scott, Murphy & Presser, P.C.

(57) ABSTRACT

The present invention relates to imidazolidinecarboxamide derivatives of the general formula I,

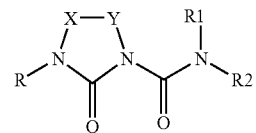

wherein R, R1, R2, X and Y are as defined herein, or pharmaceutically usable salts thereof and the use thereof as medicinal substances.

12 Claims, No Drawings

IMIDAZOLIDINE CARBOXAMIDE DERIVATIVES AS LIPASE AND PHOSPHOLIPASE INHIBITORS

This application is a Continuation of International Application No. PCT/EP2008/002231, filed Mar. 20, 2008, which is incorporated herein by reference in its entirety.

FIELD OF THE INVENTION

The present invention relates to imidazolidinecarboxamide derivatives of the general formula I, the pharmaceutically usable salts thereof and the use thereof as medicinal substances.

BACKGROUND OF THE INVENTION

Besides the imidazolidinecarboxamide derivatives described in the present application, compounds of similar structure have been described in the prior art, for example by Pirkle et al. in Chirality 4, 302-307 (1992), phenylaminocarbonyl-hydantoins in JP 11147878 as fungicides. Compounds of similar structure having a pharmacological effect are described in J. Med. Chem. 1995, 38, 923-933 as $NK_1$ receptor antagonists.

Compounds having an inhibitory effect on endothelial lipase are described in the prior art, for example in WO2004/094394, WO2004/094393, WO2004/093872 or WO2006/111321.

It is an object of the present invention to provide alternative compounds which bring about an inhibition of endothelial lipase.

SUMMARY OF THE INVENTION

The invention relates to imidazolidinecarboxamide derivatives of the general formula I

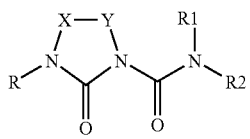

X, Y identically or differently —C(R3)(R4)-, —(C=O)—, —(C=S), where at least one X or Y is —(C=O)— or —(C=S)—; but cannot both simultaneously be —(C=O)— or —(C=S)—; or X and Y together are C(R3)=C(R3);

R hydrogen, $(C_1-C_8)$-alkyl, $(C_1-C_5)$-haloalkyl, $(CR5R6)_m$-O(R7), $(C_1-C_3)$-alkyloxy-$(C_1-C_3)$-alkylene, aryl, heterocycle, $(C_1-C_4)$-alkylene-aryl, $(C_1-C_4)$-alkylene-heteroaryl, $(C_1-C_4)$-alkylene-$(C_8-C_{12})$-cycloalkyl, where cycloalkyl, aryl, heterocycle or heteroaryl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, $(C_0-C_8)$-alkylene-aryl, O—$(C_0-C_8)$-alkylene-aryl, S-aryl, $(C_0-C_8)$-alkylene-heteroaryl, N(R5)(R6), $SO_2$—$CH_3$, $SO_2$—$NH_2$, $SF_5$, COOH, COO—$(C_1-C_6)$-alkyl, CON(R5)(R6), N(R5)CO(R6), N(R5)$SO_2$(R6), CO(R5), $(CR5R6)_{m'}$—O(R7), O—CO—N(R5)(R6), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R5)(R6), where aryl or heteroaryl may in turn be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_2-C_6)$-alkynyl, N(R8)(R9), $SO_2$—$CH_3$, $SF_5$, COOH, COO—$(C_1-C_6)$-alkyl, CON(R8)(R9), N(R8)CO(R9), N(R8)$SO_2$(R9), CO(R8), $(CR8R9)_{m''}$—O(R10), O—CO—N(R8)(R9), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R8)(R9);

m, m', m'' 0, 1, 2, 3, 4, 5, 6;

R5, R6, R7, R8, R9, R10 identically or differently hydrogen, $(C_1-C_8)$-alkyl;

or —(C=O)—NR1aR2a;

or —(C=O)—O—R1b;

or

R and X for X=—C(R3)(R4)- form a monocyclic, saturated or partly unsaturated 4- to 7-membered ring system or a bicyclic saturated or partly unsaturated 8- to 14-membered ring system whose individual members of the ring systems may be replaced by one to three atoms or atomic groups from the series —CHR11-, —CR11R12-, —(C=R11)-, =C(R11)-, —NR11-, —C(=O)—, —O—, —S—, —SO—, —$SO_2$—, with the proviso that two units from the series —O—, —S—, —SO—, —$SO_2$— may not be adjacent;

R11, R12 identically or differently hydrogen, $(C_1-C_6)$-alkyl, aryl, $(C_3-C_{12})$-cycloalkyl, $(C_1-C_4)$-alkylene-aryl, $(C_1-C_3)$-alkylene-$(C_3-C_{12})$-cycloalkyl;

where aryl or cycloalkyl may be substituted by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R13)(R14), $SO_2$—$CH_3$, $SO_2$—$NH_2$, $SF_5$, COOH, COO—$(C_1-C_6)$-alkyl, CON(R13)(R14), N(R13)CO(R14), N(R13)$SO_2$(R14), CO(R13), $(CR13R14)_n$-O(R15), O—CO—N(R13)(R14), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R13)(R14);

n 0, 1, 2, 3, 4, 5, 6;

R13, R14, R15 identically or differently hydrogen, $(C_1-C_8)$-alkyl;

R1, R1a, R1b identically or differently $(C_5-C_{16})$-alkyl, $CH_2$-aryl, $(C_1-C_2)$-alkylene-heteroaryl, $CH_2$—$(C_5-C_{12})$-cycloalkyl, where aryl, heteroaryl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, $(C_0-C_8)$-alkylene-aryl, O—$(C_0-C_8)$-alkylene-aryl, S-aryl, $(C_0-C_8)$-alkylene-heteroaryl, N(R16)(R17), $SO_2$—$CH_3$, $SO_2$—$NH_2$, $SF_5$, COOH, COO—$(C_1-C_6)$-alkyl, CON(R16)(R17), N(R16)CO(R17), N(R16)$SO_2$(R17), CO(R16), $(CR16R17)_o$O(R18), O—CO—N(R16)(R17), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R16)(R17), where aryl or heteroaryl in turn may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_2-C_6)$-alkynyl, N(R19)

(R20), $SO_2$—$CH_3$, $SF_5$, COOH, COO—$(C_1-C_6)$-alkyl, CON(R19)(R20), N(R19)CO(R20), N(R19)$SO_2$(R20), CO(R19), $(CR19R20)_o$—O(R21), O—CO—N(R19)(R20), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R19)(R20);

o, o' 0, 1, 2, 3, 4, 5, 6;

R16, R17, R18, R19, R20, R21
identically or differently hydrogen, $(C_1-C_8)$-alkyl;
or a radical of the formula Ia

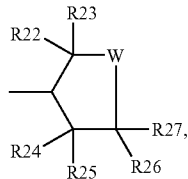

with
W —C(R28)(R29)-, —C(R28)(R29)-C(R28a)(R29a)-, —C(R28)(R29)-O—;

R22, R23, R24, R25, R26, R27, R28, R29, R28a, R29a
identically or differently hydrogen, F, Cl, Br, I, OH, $CF_3$, $NO_2$, CN, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, N(R30)(R31), $SO_2$—$CH_3$, COOH, COO—$(C_1-C_6)$-alkyl, CON(R30)(R31), N(R30)CO(R31), N(R30)$SO_2$(R31), CO(R30), $(CR30R31)_p$-O(R32), O—CO—N(R30)(R31), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R30)(R31);

P 0, 1, 2, 3, 4, 5, 6;

R30, R31, R32 identically or differently hydrogen, $(C_1-C_6)$-alkyl;
or
R22 and R28 or R23 and R29 together with the carbon atoms bearing them form a monocyclic, 5 or 6 membered saturated, partly unsaturated or aromatic ring system whose individual members may be replaced by —CHR33-, —CR33R34-, =(C—R33)-;
or
R24 and R26, or R25 and R27 together with the carbon atoms bearing them form a monocyclic, 5 or 6 membered saturated, partly unsaturated or an aromatic ring system whose individual members may be replaced by —CHR33-, —CR33R34-, =(C—R33)-;

R33, R34 identically or differently F, Cl, Br, I, OH, $CF_3$, $NO_2$, CN, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R35)(R36), $SO_2$—$CH_3$, COOH, COO—$(C_1-C_6)$-alkyl, CON(R35)(R36), N(R35)CO(R36), N(R35)$SO_2$(R36), CO(R35), $(CR35R36)_q$-O(R37), O—CO—N(R35)(R36), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R35)(R36);

q 0, 1, 2, 3, 4, 5, 6;

R35, R36, R37 identically or differently hydrogen, $(C_1-C_6)$-alkyl;

R2, R2a identically or differently hydrogen; $(C_1-C_8)$-alkyl;

R3, R4 identically or differently hydrogen, $(C_1-C_6)$-alkyl, benzyl;

the tautomeric forms of the compounds and the physiologically tolerated salts thereof;

with the proviso that R1 is not pentyl, $CH_2$-phenyl, —$CH_2$-(2-$C_1$-phenyl), cyclohexyl, -(2-methylcyclohexyl) if X=$CH_2$, Y=CO, R=methyl, R2=H.

DETAILED DESCRIPTION OF THE INVENTION

A preferred embodiment is compounds of the formula I in which R2 is hydrogen.

Compounds of the formula I in which
X is —(C=O)— and
Y is —C(R3)(R4)-;
are preferred.

Compounds of the formula I in which
Y is —(C=O)— and
X is —C(R3)(R4)-;
are also preferred.

Particularly preferred compounds of the formula I are those in which
Y is —(C=O)— and
X is —C(R3)(R4)-;
or
X is —(C=O)— and
Y is —C(R3R4)-;

R is hydrogen, $(C_1-C_8)$-alkyl, $(C_1-C_3)$-haloalkyl, $(CR5R6)_m$-O(R7), phenyl, heterocycle, $(C_1-C_4)$-alkylene-phenyl, $(C_1-C_4)$-alkylene-heteroaryl, $(C_1-C_4)$-alkylene-$(C_5-C_{12})$-cycloalkyl, where cycloalkyl, phenyl, heterocycle or heteroaryl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, $(C_0-C_8)$-alkylene-aryl, O—$(C_0-C_8)$-alkylene-aryl, S-aryl, $(C_0-C_8)$-alkylene-heteroaryl, N(R5)(R6), $SO_2$—$CH_3$, $SO_2$—$NH_2$, $SF_5$, COOH, COO—$(C_1-C_6)$-alkyl, CON(R5)(R6), N(R5)CO(R6), N(R5)$SO_2$(R6), CO(R5), $(CR5R6)_{m'}$-O(R7), O—CO—N(R5)(R6), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R5)(R6), where aryl or heteroaryl may in turn be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_8)$-alkenyl, $(C_3-C_8)$-cycloalkyl, O—$(C_3-C_8)$-cycloalkyl, $(C_2-C_6)$-alkynyl, N(R8)(R9), $SO_2$—$CH_3$, $SF_5$, COOH, COO—$(C_1-C_6)$-alkyl, CON(R8)(R9), N(R8)CO(R9), N(R8)$SO_2$(R9), CO(R8), $(CR8R9)_{m''}$-O(R10), O—CO—N(R8)(R9), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R8)(R9);

m, m', m" are 0, 1, 2, 3, 4, 5, 6;

R5, R6, R7, R8, R9, R10
are identically or differently hydrogen, $(C_1-C_6)$-alkyl;
or —(C=O)—NR1aR2a;
or —(C=O)—O—R1b;
or
R and X for X=—C(R3)(R4)- form a monocyclic, saturated 5- to 7-membered ring system or a bicyclic partly unsaturated 8- to 14 membered ring system whose individual members may be replaced by one to three atoms or atomic groups from the series —CHR11-, —CR11R12-, —(C=R11)-, —NR11-, —C(=O)—, —O—, with the proviso that two units from the series —O— may not be adjacent;

R11, R12 are identically or differently hydrogen, $(C_1-C_6)$-alkyl, phenyl, $(C_3-C_{12})$-cycloalkyl, $(C_1-C_4)$-alkylene-phenyl, $(C_1-C_3)$-alkylene-$(C_3-C_{12})$—cycloalkyl;
  where phenyl or cycloalkyl may be substituted by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_2-C_6)$-alkynyl, N(R13)(R14), $SO_2$—$CH_3$, $SO_2$—$NH_2$, $SF_5$, COOH, COO—$(C_1-C_6)$-alkyl, CON(R13)(R14), N(R13)CO(R14), N(R13)$SO_2$(R14), CO(R13), (CR13R14)$_n$-O(R15), O—CO—N(R13)(R14), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R13)(R14);

n is 0, 1, 2, 3, 4, 5, 6;
R13, R14, R15 are independently of one another hydrogen, $(C_1-C_8)$-alkyl;
R1, R1a, R1b are identically or differently $(C_5-C_{12})$-alkyl, —$CH_2$-phenyl, $(C_1-C_2)$-alkylene-heteroaryl, —$CH_2$—$(C_5-C_{12})$-cycloalkyl, $(C_5-C_6)$-cycloalkyl, where phenyl, heteroaryl or cycloalkyl may be substituted one or more times by F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, $(C_0-C_8)$-alkylene-phenyl, O—$(C_0-C_8)$-alkylene-phenyl, S-phenyl, $(C_0-C_8)$-alkylene-heteroaryl, N(R16)(R17), $SO_2$—$CH_3$, $SO_2$—$NH_2$, $SF_5$, COOH, COO—$(C_1-C_6)$-alkyl, CON(R16)(R17), N(R16)CO(R17), N(R16)$SO_2$(R17), CO(R16), (CR16R17)$_o$-O(R18), O—CO—N(R16)(R17), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R16)(R17), where phenyl or heteroaryl may in turn be substituted one or more times by
  F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_2-C_6)$-alkynyl, N(R19)(R20), $SO_2$—$CH_3$, $SF_5$, COOH, COO—$(C_1-C_6)$-alkyl, CON(R19)(R20), N(R19)CO(R20), N(R19)$SO_2$(R20), CO(R19), (CR19R20)$_o$-O(R21), O—CO—N(R19)(R20), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R19)(R20);

o, o' are 0, 1, 2, 3, 4, 5, 6;
R16, R17, R18, R19, R20, R21
  are identically or differently hydrogen, $(C_1-C_8)$-alkyl;
  or a radical of the formula Ib

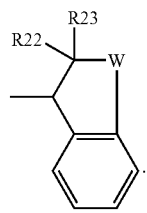

Very particularly preferred compounds of the formula I are those in which

Y is —(C=O)— and
X is —C(R3)(R4)-;
or
X is —(C=O)— and
Y is —C(R3)(R4)-;
R is hydrogen, $(C_1-C_8)$-alkyl, $(CR5R6)_m$-O(R7), phenyl, —$CH_2$-phenyl, where phenyl may be substituted once or twice by F, Cl, Br, $CF_3$, O—$(C_1-C_6)$-alkyl, $(C_1-C_6)$-alkyl, O—$(C_2-C_4)$-haloalkyl, N(R5)(R6), $SO_2$—$CH_3$, $SO_2$—$NH_2$, COOH, COO—$(C_1-C_6)$-alkyl, CON(R5)(R6), CO(R5), $(CR5R6)_{m'}$-O(R7),
m, m' are 0, 1, 2, 3;
R5, R6, R7
  are identically or differently hydrogen, $(C_1-C_8)$-alkyl;
or
R and X for X=—C(R3)(R4)- form a monocyclic, saturated 6-membered ring system or a bicyclic partly unsaturated 9- to 11-membered ring system whose individual members may be replaced by one to two atoms or atomic groups from the series —CHR11-, —CR11R12-, —(C=R11)-, =C(R11)-;
R11, R12 are identically or differently hydrogen, $(C_1-C_6)$-alkyl;
R1 is $(C_5-C_8)$-alkyl, —$CH_2$-phenyl, $(C_1-C_2)$-alkylene-heteroaryl, where heteroaryl is selected from the group of thiophene, benzothiophene, pyridine, pyrazole, —$CH_2$—$(C_5-C_7)$-cycloalkyl, $(C_5-C_6)$-cycloalkyl, where phenyl, heteroaryl or cycloalkyl may be substituted one or more times by F, Cl, Br, OH, $CF_3$, $NO_2$, CN, $OCF_3$, O—$(C_1-C_6)$-alkyl, $(C_1-C_6)$-alkyl, $(C_0-C_8)$-alkylene-phenyl, O—$(C_0-C_8)$-alkylene-phenyl, $(C_0-C_8)$-alkylene-heteroaryl, N(R16)(R17), $SO_2$—$CH_3$, $SO_2$—$NH_2$, COOH, COO—$(C_1-C_6)$-alkyl, CON(R16)(R17), CO(R16), (CR16R17)$_o$-O(R18), where phenyl or heteroaryl may in turn be substituted one or more times by
  F, Cl, Br, OH, $CF_3$, $NO_2$, CN, $OCF_3$, O—$(C_1-C_6)$-alkyl, $(C_1-C_6)$-alkyl, COOH, COO—$(C_1-C_6)$-alkyl, CON(R19)(R20), CO(R19), (CR19R20)$_o$—O(R21);
o, o' are 0, 1, 2, 3;
R16, R17, R18, R19, R20, R21
  are identically or differently hydrogen, $(C_1-C_8)$-alkyl;
  or a radical from the group

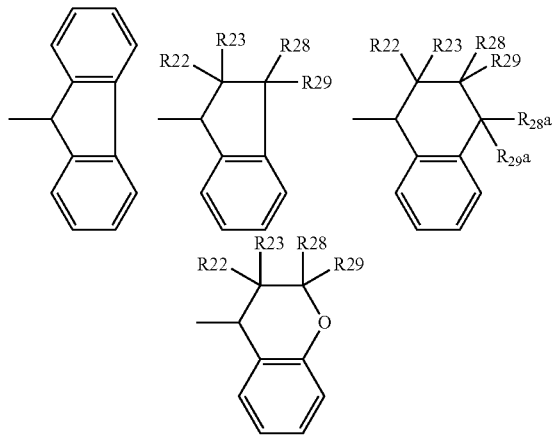

R22, R23, R28, R29, R28a, R29a are identically or differently hydrogen, $(C_1-C_6)$-alkyl, preferably hydrogen and methyl;
R2 is hydrogen;
R3, R4 are identically or differently hydrogen, methyl.
Further particularly preferred compounds of the formula I are those in which Y is —(C=O)— and
X is —C(R3)(R4)-;
or
X is —(C=O)— and
Y is —C(R3(R4)-;
R is hydrogen, (C$_1$-C$_8$)-alkyl, (CR5R6)$_m$-O(R7), —CH$_2$-phenyl, where phenyl may be substituted once or twice by F, Cl, Br, CF$_3$, O—(C$_1$-C$_6$)-alkyl, (C$_1$-C$_6$)-alkyl, O—(C$_2$-C$_4$)-haloalkyl, COOH, COO—(C$_1$-C$_6$)-alkyl, CON(R5)(R6), CO(R5), (CR5R6)$_{m'}$-O(R7),
m, m' are 0, 1, 2, 3;
R5, R6, R7
are identically or differently hydrogen, (C$_1$-C$_4$)-alkyl;
or
R and X for X=—C(R3)(R4)- form a monocyclic, saturated 6-membered ring system to which a benzene nucleus may be fused, whose individual members of the ring systems may be replaced by one to two atomic groups from the series —CHR11-, —CR11R12-, —(C=R11)-, =C(R11)-;
R11, R12 are identically or differently hydrogen, (C$_1$-C$_6$)-alkyl;
R1 is (C$_5$-C$_8$)-alkyl, —CH$_2$-phenyl, (C$_1$-C$_2$)-alkylene-heteroaryl, where heteroaryl is selected from the group of thiophene, benzothiophene, —CH$_2$-cyclohexyl, cyclohexyl, where phenyl, heteroaryl or cyclohexyl may be substituted once or twice by F, Cl, OH, CF$_3$, OCF$_3$, O—(C$_1$-C$_6$)-alkyl, (C$_1$-C$_6$)-alkyl, (C$_0$-C$_1$)-alkylene-phenyl, O-phenyl, (C$_0$-C$_1$)-alkylene-heteroaryl, N(R16)(R17), COOH, COO—(C$_1$-C$_6$)-alkyl, CON(R16)(R17), CO(R16), (CR16R17)$_o$-O(R18), where phenyl or heteroaryl may in turn be substituted once or twice by F, Cl, OH, CF$_3$, O—(C$_1$-C$_6$)-alkyl, (C$_1$-C$_6$)-alkyl, COOH, COO—(C$_1$-C$_6$)-alkyl, CON(R19)(R20), CO(R19), (CR19R20)$_o$-O(R21);
o, o' are 0, 1, 2, 3;
R16, R17, R18, R19, R20, R21
are identically or differently hydrogen, (C$_1$-C$_8$)-alkyl;
or a radical from the group

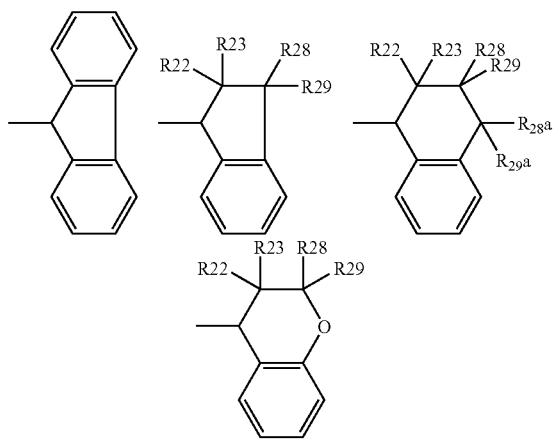

R22, R23, R28, R29, R28a, R29a are identically or differently hydrogen, (C$_1$-C$_6$)-alkyl, preferably hydrogen and methyl;
R2 is hydrogen;
R3, R4 are identically or differently hydrogen, methyl.
Particularly preferred compounds of the formula I are in particular those in which
Y is —(C=O)— and
X is —C(R3)(R4)-;
or
X is —(C=O)— and
Y is —C(R3)(R4)-;
R is hydrogen, methyl, n-butyl, HO—CH$_2$—, benzyl,
or
R and X for X=—C(—R3)(R4)- form —CH$_2$—CH$_2$—CH$_2$—CH$_2$— or

;

R1 is pentyl, hexyl, heptyl, cyclohexyl, —CH$_2$-cyclohexyl, —CH$_2$-phenyl, —CH$_2$-thiophene, —CH$_2$—CH$_2$-thiophene, where cyclohexyl, phenyl or thiophene may be substituted by methyl;
or a radical from the group

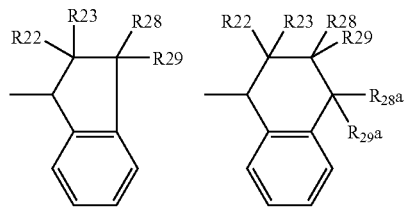

R22, R23, R28, R29, R28a, R29a are hydrogen;
R2 is hydrogen;
R3, R4 are identically or differently hydrogen, methyl.

The invention relates to compounds of the formula I in the form of their salts, racemates, racemic mixtures and pure enantiomers, and to their diastereomers and mixtures thereof.

If radicals or substituents may occur more than once in the compounds of the formula I, they may all independently of one another have the stated meanings and be identical or different.

The alkyl or alkylene radicals in the substituents R, R1 to R37 may be either straight chain or branched. Halogen is fluorine, chlorine, bromine or iodine, in particular fluorine or chlorine.

Haloalkyl is an alkyl which is substituted one or more times or completely by halogen. Preferred halogens are fluorine and chlorine.

A cycloalkyl radical means a ring system which comprises one or more rings, which is saturated or partly unsaturated (having one or two double bonds) and which is composed exclusively of carbon atoms, such as, for example, cyclopropyl, cyclopentyl, cyclopentenyl, cyclohexyl or adamantyl.

The cycloalkyl radicals may be substituted one or more times by suitable groups such as, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CONR[(C$_1$-C$_6$)alkyl]$_2$, cycloalkyl, (C$_1$-C$_{10}$)-alkyl, (C$_2$-C$_6$)-alkenyl, (C$_2$-C$_6$)-alkynyl, O—(C$_1$-C$_6$)-alkyl O—CO—(C$_1$-C$_6$)-alkyl, O—CO—(C$_1$-C$_6$)-aryl, O—CO—(C$_1$-C$_6$)-heterocycle;
PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N(C$_1$-C$_6$)-alkyl)(CH$_2$)$_n$-aryl, SO$_2$—N(C$_1$-C$_6$)- alkyl)(CH$_2$)$_n$-heterocycle, SO$_2$—N((CH$_2$)$_n$-aryl)$_2$, SO$_2$—N((CH$_2$)$_n$-(heterocycle)$_2$, where n may be 0-6, and the aryl radical or heterocyclic radical may be substituted up to twice by F, Cl, Br, OH, CF$_3$, NO$_2$, CN, OCF$_3$, O—(C$_1$-C$_6$)-alkyl, (C$_1$-C$_6$)-alkyl, NH$_2$;
C(NH)(NH$_2$), NH$_2$, NH—(C$_1$-C$_6$)-alkyl, N((C$_1$-C$_6$)-alkyl)$_2$, NH(C$_1$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N(C$_1$-C$_6$)-alkyl-CO—(C$_1$-C$_6$)-alkyl, N(C$_1$-C$_6$)-alkyl-COO—(C$_1$-C$_6$)-alkyl, N(C$_1$-C$_6$)-alkyl-CO-aryl, N(C$_1$-C$_6$)-alkyl-CO-heterocycle, N(C$_1$-C$_6$)-alkyl-COO-aryl, N(C$_1$-C$_6$)-alkyl-COO-heterocycle, N(C$_1$-C$_6$)-alkyl-CO—NH—(C$_1$-C$_6$)-alkyl), N(C$_1$-C$_6$)-alkyl-CO—NH-aryl, N(C$_1$-C$_6$)-alkyl-CO—NH-heterocycle, N((C$_1$-C$_6$)-alkyl)-CO—N—(C$_1$-C$_6$)-alkyl)$_2$, N((C$_1$-C$_6$)-alkyl)-CO—N((C$_1$-C$_6$)-alkyl)aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N—(C$_1$-C$_6$)-alkyl)$_2$, N(heterocycle)-CO—N—(C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to three times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$.

An aryl radical means a phenyl or naphthyl radical.

The aryl radicals may be substituted one or more times by suitable groups such as, for example: F, Cl, Br, I, CF$_3$, NO$_2$, CN, COOH, COO(C$_1$-C$_6$)alkyl, CONH$_2$, CONH(C$_1$-C$_6$)alkyl, CON[(C$_1$-C$_6$)alkyl]$_2$, (C$_3$-C$_{10}$)-cycloalkyl, (C$_1$-C$_{10}$)-alkyl, (C$_2$-C$_6$)-alkenyl, (C$_2$-C$_6$)-alkynyl, O—(C$_1$-C$_6$)-alkyl O—CO—(C$_1$-C$_6$)-alkyl, O—CO—(C$_1$-C$_6$)-aryl, PO$_3$H$_2$, SO$_3$H, SO$_2$—NH$_2$, SO$_2$NH(C$_1$-C$_6$)-alkyl, SO$_2$N[(C$_1$-C$_6$)-alkyl]]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N(C$_1$-C$_6$)-alkyl)(CH$_2$)$_n$-aryl, SO$_2$—N(C$_1$-C$_6$)-alkyl)(CH$_2$)$_n$-heterocycle, SO$_2$—N((CH$_2$)$_n$-aryl)$_2$, SO$_2$—N((CH$_2$)$_n$-(heterocycle)$_2$, where n may be 0-6, and the aryl radical or heterocyclic radical may be substituted up to twice by F, Cl, Br, OH, CF$_3$, NO$_2$, CN, OCF$_3$, O—(C$_1$-C$_6$)-alkyl, (C$_1$-C$_6$)-alkyl, NH$_2$;
C(NH)(NH$_2$), NH$_2$, NH—(C$_1$-C$_6$)-alkyl, N((C$_1$-C$_6$)-alkyl)$_2$, NH(C$_1$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N(C$_1$-C$_6$)-alkyl-CO—(C$_1$-C$_6$)-alkyl, N(C$_1$-C$_6$)-alkyl-COO—(C$_1$-C$_6$)-alkyl, N(C$_1$-C$_6$)-alkyl-CO-aryl, N(C$_1$-C$_6$)-alkyl-CO-heterocycle, N(C$_1$-C$_6$)-alkyl-COO-aryl, N(C$_1$-C$_6$)-alkyl-COO-heterocycle, N(C$_1$-C$_6$)-alkyl-CO—NH—(C$_1$-C$_6$)-alkyl), N(C$_1$-C$_6$)-alkyl-CO—NH-aryl, N(C$_1$-C$_6$)-alkyl-CO—NH-heterocycle, N((C$_1$-C$_6$)-alkyl)-CO—N—(C$_1$-C$_6$)-alkyl)$_2$, N((C$_1$-C$_6$)-alkyl)-CO—N((C$_1$-C$_6$)-alkyl)aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N—(C$_1$-C$_6$)-alkyl)$_2$, N(heterocycle)-CO—N—(C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl, O—(CF$_{12}$)$_n$-heterocycle, where n may be 0-6, where the aryl radical or heterocyclic radical may be substituted one to three times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$.

Heterocycle is a mono- or bicyclic ring system having 5 to 12 ring members in which at least one atom in the ring system is a heteroatom from the series N, O and S. This definition also includes ring systems in which the heterocycle is fused to a benzene nucleus. (C$_5$-C$_7$)-heterocycle is a monocyclic, (C$_8$-C$_{12}$)-heterocycle is a bicyclic ring system.

Suitable "heterocyclic rings" or "heterocyclic radicals" are azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyrazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadiazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is both 2-, 3- and 4-pyridyl. Thienyl is both 2- and 3-thienyl. Furyl is both 2- and 3-furyl.

Also included are the corresponding N-oxides of these compounds, i.e. for example 1-oxy-2-, 3- or 4-pyridyl.

The heterocyclic rings or heterocyclic radicals may be substituted one or more times by suitable groups such as, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, (C$_1$-C$_6$)-alkyl, (C$_2$-C$_6$)-alkenyl, (C$_2$-C$_6$)-alkynyl, O—(C$_1$-C$_6$)-alkyl, where one, more than one, or all hydrogen(s) in the alkyl radicals may be replaced by fluorine; PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-phenyl, SO—(C$_1$-C$_6$)-alkyl, SO—(CH$_2$)$_n$-phenyl, SO$_2$—(C$_1$-C$_6$)-alkyl, SO$_2$—(CH$_2$)$_n$-phenyl, where n may be 0-6, and the phenyl radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

$C(NH)(NH_2)$, $NH_2$, NH—$(C_1$-$C_6)$-alkyl, $N((C_1$-$C_6)$-alkyl$)_2$, $NH(C_1$-$C_7)$-acyl, phenyl, O—$(CH_2)_n$-phenyl, where n may be 0-6, where the phenyl ring may be substituted one to three times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl$)_2$, $SO_2$—$CH_3$, COOH, COO—$(C_1$-$C_6)$-alkyl, $CONH_2$.

Heteroaryl is a mono- or bicyclic aromatic ring system having 5 to 12 ring members, in which at least one atom in the ring system is a heteroatom from the series N, O and S. This definition also includes ring systems in which the heteroaryl is fused to a benzene nucleus.

Suitable "heteroaryl rings" or "heteroaryl radicals" are for example benzimidazolyl, benzofuranyl, benzothiophenyl, benzoxazolyl, benzthiazolyl, benztriazolyl, benztetrazolyl, benzisoxazolyl, benzisothiazolyl, quinolinyl, furyl, furazanyl, imidazolyl, 1H-indazolyl, indolyl, 1,2,3-oxadiazolyl, 1,2,4-oxadiazolyl, 1,2,5-oxadiazolyl, 1,3,4-oxadiazolyl, pyrimidinyl, pyrazinyl, pyrazolyl, pyridyl, pyrrolyl, thiazolyl, 1,2,3-thiadiazolyl, 1,2,4-thiadiazolyl, 1,2,5-thiadiazolyl, 1,3,4-thiadiazolyl, thiophenyl.

The heteroaryl rings or heteroaryl radicals may be substituted one or more times by suitable groups such as, for example: F, Cl, Br, I, $CF_3$, $NO_2$, $N_3$, CN, COOH, $COO(C_1$-$C_6)$alkyl, $CONH_2$, $CONH(C_1$-$C_6)$alkyl, $CON[(C_1$-$C_6)$ alkyl$]_2$, $(C_1$-$C_6)$-alkyl, $(C_2$-$C_6)$-alkenyl, $(C_2$-$C_6)$-alkynyl, O—$(C_1$-$C_6)$-alkyl, where one, more than one, or all hydrogen(s) in the alkyl radicals may be replaced by fluorine;

$PO_3H_2$, $SO_3H$, $SO_2$—$NH_2$, $SO_2NH(C_1$-$C_6)$-alkyl, $SO_2N[(C_1$-$C_6)$-alkyl$]_2$, S—$(C_1$-$C_6)$-alkyl, S—$(CH_2)_n$-phenyl, SO—$(C_1$-$C_6)$-alkyl, SO—$(CH_2)_n$-phenyl, $SO_2$—$(C_1$-$C_6)$-alkyl, $SO_2$—$(CH_2)_n$-phenyl, where n may be 0-6, and the phenyl radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

$C(NH)(NH_2)$, $NH_2$, NH—$(C_1$-$C_6)$-alkyl, $N((C_1$-$C_6)$-alkyl$)_2$, $NH(C_1$-$C_7)$-acyl, phenyl, O—$(CH_2)_n$-phenyl, where n may be 0-6, where the phenyl ring may be substituted one to three times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl$)_2$, $SO_2$—$CH_3$, COOH, COO—$(C_1$-$C_6)$-alkyl, $CONH_2$.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the invention of the formula I, for example an ester, which on administration to a mammal such as, for example, a human is able to form (directly or indirectly) a compound of the formula I or an active metabolite thereof.

Physiologically functional derivatives also include prodrugs of the compounds of the invention such as, for example, described in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

The compounds of the formula I have a surprising inhibitory effect on endothelial lipase (EL). The preferred substrate for EL is HDL, which has antiatherosclerotic activity. A reduction in the HDL level leads to progression of atherosclerosis and its sequelae such as coronary heart disease, and additionally favors the development of metabolic syndrome and its sequela diabetes. An inhibition of EL should thus lead generally to prevention of atherosclerotic disorders, and indirectly reduce the probability of disease in people with an increased risk for diabetes.

It has further been found that the inhibitory effect of the compounds of the invention of the formula I is selective in relation to other lipases.

The compounds of the formula I additionally show an improved solubility in aqueous media while having an activity which is at least as high as compounds of similar structures. The compounds of the invention are further distinguished by further advantageous properties such as higher metabolic stability and serum stability compared with prior art compounds.

Compounds of this type are particularly suitable for the treatment and/or prevention of 1. Dyslipidemias and general disorders of lipid metabolism and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations
   low HDL cholesterol concentration
   low apoA lipoprotein concentrations
   high LDL cholesterol concentrations
   small dense LDL cholesterol particles
   high apoB lipoprotein concentrations
2. Various other conditions which may be associated with the metabolic syndrome, such as:
   obesity (excess weight), including central obesity
   thromboses, hypercoagulable and prothrombotic stages (arterial and venous)
   high blood pressure
   heart failure such as, for example (but not restricted thereto), following myocardial infarction, hypertensive heart disease or cardiomyopathy
   diabetes mellitus, especially type 2 diabetes, including the prevention of the sequelae associated therewith (hyperglycemia, glucose intolerance, loss of the pancreatic β cells, macro- and microvascular disorders)
3. Other disorders or conditions in which inflammatory reactions or cell differentiation is for example involved are:
atherosclerosis such as, for example (but not restricted thereto), coronary sclerosis including angina pectoris or myocardial infarction, stroke
vascular restenosis or reocclusion
chronic inflammatory bowel diseases such as, for example, Crohn's disease and ulcerative colitis
pancreatitis
other inflammatory states
retinopathy
adipose cell tumors
adipose cell carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions which are modulated by PPAR
eczemas and neurodermatitis
dermatitis such as, for example, seborrheic dermatitis or photodermatitis keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal papillomata, viral warts such as, for example, molluscum contagiosum, leukoplakia
papular dermatoses such as, for example, lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)
Formulations The amount of a compound of the invention necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of the invention. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on lipid metabolism disorders. They beneficially influence the ratio of HDL to LDL and in particular increase the HDL level and are suitable for the prevention and treatment of dyslipidemias and metabolic syndrome and the diverse sequelae thereof such as atherosclerosis, coronary heart disease, heart failure, obesity and diabetes.

Combinations with Other Medicaments

The compounds of the invention can be administered alone or in combination with one or more further pharmacologically active ingredients. In particular the compounds of the invention can be administered with active ingredients, which have a similar pharmacological effect to themselves. For example, they can be administered in combination with active ingredients which have favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
11. active ingredients for the treatment of neurodegenerative diseases
12. active ingredients for the treatment of diseases of the central nervous system
13. active ingredients for the treatment of dependence on drugs, nicotine and alcohol
14. analgesics They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further active ingredients particularly suitable for the combination products are: All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They can be combined with the compound of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or those described in WO 2005005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1-derivatives such as, for example, exenatide, liraglutide or those which have been disclosed in WO 98/08871 or WO 2005027978 of Novo Nordisk A/S, in WO 01/04156 of Zealand or in WO 00/34331 of Beaufour-Ipsen, pramlintide acetate (Symlin; Amylin Pharmaceuticals), and orally effective hypoglycemic active ingredients.

The active ingredients include preferably
sulfonylureas,
biguanides,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists,
potassium channel openers such as, for example, those which have been disclosed in WO 97/26265 and WO 99/03861 of Novo Nordisk NS,
inhibitors of dipeptidylpeptidase IV (DPP-IV), insulin sensitizers,
inhibitors of liver enzymes involved in stimulating gluconeogenesis and/or
glycogenolysis,
modulators of glucose uptake, of glucose transport and of glucose reabsorption, inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO 2005042692), MD-0727 (Microbia Inc., WO 2005021497) or with compounds as described in WO 2002066464 (Kotobuki Pharmaceutical Co. Ltd.), WO 2005062824 (Merck & Co.) or WO 2005061451 and WO 2005061452 (AstraZeneca AB).

In one embodiment of the invention, the compound of the formula I is administered in combination with a PPAR gamma agonist such as, for example, rosiglitazone, pioglitazone, JTT-501, GI 262570, R-483 or CS-011 (rivoglitazone).

In one embodiment of the invention, the compound of the formula I is administered in combination with a PPAR alpha agonist such as, for example, GW9578, GW-590735, K-111, LY-674, KRP-101 or DRF-10945.

In one embodiment of the invention, the compound of the formula I is administered in combination with a mixed PPAR alpha/gamma agonist such as, for example, muraglitazar, tesaglitazar, naveglitazar, LY-510929, ONO-5129, E-3030 or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757 or those described in WO 2005085226.

In one embodiment of the invention, the compound of the formula I is administered in combination with a CETP inhibitor such as, for example, torcetrapib or JTT-705.

In one embodiment of the invention, the compound of the formula I is administered in combination with a bile acid absorption inhibitor (see, for example, U.S. Pat. No. 6,245,744, U.S. Pat. No. 6,221,897 or WO 00/61568), such as, for example, HMR 1741 or those as described in DE 10 2005 033099.1 and DE 10 2005 033100.9.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO 2005097738.

In one embodiment, the compound of the formula I is administered in combination with Omacor® (Omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO 2005077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an HM74A receptor agonist such as, for example, nicotinic acid.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment of the invention, the compound of the formula I is administered in combination with a sulfonylurea such as, for example, tolbutamide, glibenclamide, glipizide or glimepiride.

In one embodiment of the invention, the compound of the formula I is administered in combination with a biguanide such as, for example, metformin.

In another embodiment of the invention, the compound of the formula I is administered in combination with a meglitinide such as, for example, repaglinide or nateglinide.

In one embodiment of the invention, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with an α-glucosidase inhibitor such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those as described in WO 2003084922, WO 2004007455, WO 2005073229-31 or WO 2005067932.

In one embodiment of the invention, the compound of the formula I is administered in combination with glucagon receptor antagonists such as, for example, A-770077, NNC-25-2504 or as described in WO 2004100875 or WO 2005065680.

In one embodiment of the invention, the compound of the formula I is administered in combination with activators of glucokinase, such as, for example, RO-4389620, LY-2121260 (WO 2004063179), PSN-105, PSN-110, GKA-50 or those as are described for example by Prosidion in WO 2004072031, WO 2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, US 04067939 or WO 04052869, by Novo Nordisk in EP 1532980, WO 03055482, WO 04002481, WO 05049019, WO 05066145 or WO 05123132, by Merck/Banyu in WO 03080585, WO 03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine-fructose-6-phosphate amidotransferase (GFAT), as are described for example in WO 2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964X or as are described in WO 2003074500, WO 2003106456, WO 200450658, WO 2005058901, WO 2005012312, WO 2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase 1 (11β-HSD1), such as, for example, BVT-2733 or those as are described for example in WO 200190090-94, WO 200343999, WO 2004112782, WO 200344000, WO 200344009, WO 2004112779, WO 2004113310, WO 2004103980, WO 2004112784, WO 2003065983, WO 2003104207, WO 2003104208, WO 2004106294, WO 2004011410, WO 2004033427, WO 2004041264, WO 2004037251, WO 2004056744, WO 2004065351, WO 2004089367, WO 2004089380, WO 2004089470-71, WO 2004089896, WO 2005016877 or WO 2005097759.

In one embodiment of the invention, the compound of the formula I is administered in combination with inhibitors of protein tyrosine phosphatase 1B (PTP1B), as are described for example in WO 200119830-31, WO 200117516, WO 2004506446, WO 2005012295, PCT/EP2005/005311, PCT/EP2005/005321, PCT/EP2005/007151, PCT/EP2005/or DE 10 2004 060542.4.

In one embodiment of the invention, the compound of the formula I is administered in combination with modulators of the sodium-dependent glucose transporter 1 or 2 (SGLT1, SGLT2), such as, for example, KGA-2727, T-1095 and SGL-0010 or as are described for example in WO 2004007517, WO 200452903, WO 200452902, WO 2005121161, WO 2005085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL) as described for example in WO 2005073199, WO 2006111321, WO 2006131233, WO 2006131232, WO 2006131231, WO 2007042178 or WO 2007045392.

In one embodiment of the invention, the compound of the formula I is administered in combination with inhibitors of acetyl-CoA carboxylase (ACC), such as, for example, those as described in WO 199946262, WO 200372197, WO 2003072197 or WO 2005044814.

In one embodiment of the invention, the compound of the formula I is administered in combination with an inhibitor of phosphoenolpyruvate carboxykinase (PEPCK), such as, for example, those as described in WO 2004074288.

In one embodiment of the invention, the compound of the formula I is administered in combination with an inhibitor of glycogen synthase kinase 3 beta (GSK-3 beta), as described for example in US2005222220, WO 2005085230, PCT/EP2005/005346, WO 2003078403, WO 2004022544, WO 2003106410, WO 2005058908, US2005038023, WO 2005009997, US2005026984, WO 2005000836, WO 2004106343, EP1460075, WO 2004014910, WO 2003076442, WO 2005087727 or WO 2004046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin A receptor antagonist such as, for example, avosentan (SPP-301).

In one embodiment of the invention, the compound of the formula I is administered in combination with inhibitors of "I-kappaB kinase" (IKK inhibitors), as are described for example in WO 2001000610, WO 2001030774, WO 2004022553 or WO 2005097129.

In one embodiment of the invention, the compound of the formula I is administered in combination with modulators of the glucocorticoid receptor, like those described for example in WO 2005090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558); NPY antagonists such as, for example, naphthalene-1-sulfonic acid {4-[(4-amino-quinazolin-2-ylamino)methyl]cyclohexylmethyl}amide hydrochloride (CGP 71683A); peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO 2005080424;

cannabinoid receptor 1 antagonists such as, for example, rimonabant, SR147778 or those as are described for example in EP 0656354, WO 00/15609, WO 02/076949, WO 2005080345, WO 2005080328, WO 2005080343, WO 2005075450, WO 2005080357, WO 200170700, WO 2003026647-48, WO 200302776, WO 2003040107, WO 2003007887, WO 2003027069, U.S. Pat. No. 6,509,367, WO 200132663, WO 2003086288, WO 2003087037, WO 2004048317, WO 2004058145, WO 2003084930, WO 2003084943, WO 2004058744, WO 2004013120, WO 2004029204, WO 2004035566, WO 2004058249, WO 2004058255, WO 2004058727, WO 2004069838, US20040214837, US20040214855, US20040214856, WO 2004096209, WO 2004096763, WO 2004096794, WO 2005000809, WO 2004099157, US20040266845, WO 2004110453, WO 2004108728, WO 2004000817, WO 2005000820, US20050009870, WO 200500974, WO 2004111033-34, WO 200411038-39, WO 2005016286, WO 2005007111, WO 2005007628, US20050054679, WO 2005027837, WO 2005028456, WO 2005063761-62, WO 2005061509 or WO 2005077897;

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO 2005060985, WO 2005009950, WO 2004087159, WO 2004078717, WO 2004078716, WO 2004024720, US20050124652, WO 2005051391, WO 2004112793, WOUS20050222014, US20050176728, US20050164914, US20050124636, US20050130988, US20040167201, WO 2004005324, WO 2004037797, WO 2005042516, WO 2005040109, WO 2005030797, US20040224901, WO 200501921, WO 200509184, WO 2005000339, EP1460069, WO 2005047253, WO 2005047251, EP1538159, WO 2004072076 or WO 2004072077;

orexin receptor antagonists (e.g. 1-(2-methylbenzoxazol-6-yl)-3-[1,5]naphthyridin-4-ylurea hydrochloride (SB-334867-A) or those as are described for example in WO 200196302, WO 200185693, WO 2004085403 or WO 2005075458); histamine H3 receptor agonists (e.g. 3-cyclohexyl-1-(4,4-dimethyl-1,4,6,7-tetrahydro-imidazo[4,5-c]pyridin-5-yl)propan-1-one oxalic acid salt (WO 00/63208) or those as are described in WO 200064884, WO 2005082893);

CRF antagonists (e.g. [2-methyl-9-(2,4,6-trimethylphenyl)-9H-1,3,9-triazafluoroen-4-yl]dipropylamine (WO 00/66585));

CRF BP antagonists (e.g. urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO 200315769, WO 2005085200, WO 2005019240, WO 2004011438, WO 2004012648, WO 2003015769, WO 2004072025, WO 2005070898, WO 2005070925, WO 2004039780, WO 2003033476, WO 2002006245, WO 2002002744, WO 2003004027 or FR2868780);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, APD-356, BVT-933 or those as are described in WO 200077010, WO 20077001-02, WO 2005019180, WO 2003064423, WO 200242304 or WO 2005082859);

5-HT6 receptor antagonists as are described for example in WO 2005058858;

bombesin receptor agonists (BRS-3 agonists);

galanin receptor antagonists;

growth hormone (e.g. human growth hormone or AOD-9604);

growth hormone releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO 2005030734;

TRH agonists (see, for example, EP 0 462 884);

uncoupling protein 2 or 3 modulators;

leptin agonists (see, for example, Lee, Daniel W.; Leinung, Matthew C.;

Rozhayskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO 2004094618, WO 200058491, WO 2005044250, WO 2005072740, JP2005206492 or WO 2005013907;

inhibitors of fatty acid synthase (FAS) such as, for example, C75 or those as described in WO 2004005277;

oxyntomodulin;

oleoyl-estrone;

or thyroid hormone receptor agonists such as, for example: KB-2115 or those as described in WO 20058279, WO 200172692, WO 200194293, WO 2003084915, WO 2004018421 or WO 2005092316.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindole or phentermine.

In one embodiment of the invention, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hoechst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE inhibitors (phosphodiesterase), like those described for example in WO 2003/077949 or WO 2005012485.

In one embodiment of the invention, the compound of the formula I is administered in combination with NAR-1 (nicotinic acid receptor) agonists like those described for example in WO 2004094429.

In one embodiment of the invention, the compound of the formula I is administered in combination with CB2 (cannabinoid receptor) agonists like those described for example in US2005/143448.

In one embodiment of the invention, the compound of the formula I is administered in combination with histamine 1 agonists like those described for example in WO 2005101979.

In one embodiment of the invention, the compound of the formula I is administered in combination with bupropion as described in WO 2006017504.

In one embodiment of the invention, the compound of the formula I is administered in combination with opioid antagonists like those described for example in WO 2005107806 or WO 2004094429.

In one embodiment of the invention, the compound of the formula I is administered in combination with neutral endopeptidase inhibitors like those described for example in WO 200202513, WO 2002/06492, WO 2002040008, WO 2002040022 or WO 2002047670.

In one embodiment of the invention, the compound of the formula I is administered in combination with NPY inhibitors (neuropeptide Y) like those described for example in WO 2002047670.

In one embodiment of the invention, the compound of the formula I is administered in combination with sodium/hydrogen exchange inhibitors like those described for example in WO 2003092694.

In one embodiment of the invention, the compound of the formula I is administered in combination with modulators of the glucocorticoid receptor like those described for example in WO 2005090336.

In one embodiment of the invention, the compound of the formula I is administered in combination with nicotine receptor agonists like those described for example in WO 2004094429.

In one embodiment of the invention, the compound of the formula I is administered in combination with NRIs (norepinephrine reuptake inhibitors) like those described for example in WO 2002053140.

In one embodiment of the invention, the compound of the formula I is administered in combination with MOA (E-beta-methoxyacrylate) such as, for example, segeline or like those described for example in WO 2002053140.

In one embodiment of the invention, the compound of the formula I is administered in combination with antithrombotic active ingredients such as, for example, clopidogrel.

It will be appreciated that every suitable combination of the compounds of the invention with one or more of the aforementioned compounds and optionally one or more other pharmacologically active substances is regarded as falling within the protection conferred by the present invention.

Some of the formulae for the development codes mentioned above are detailed hereinafter.

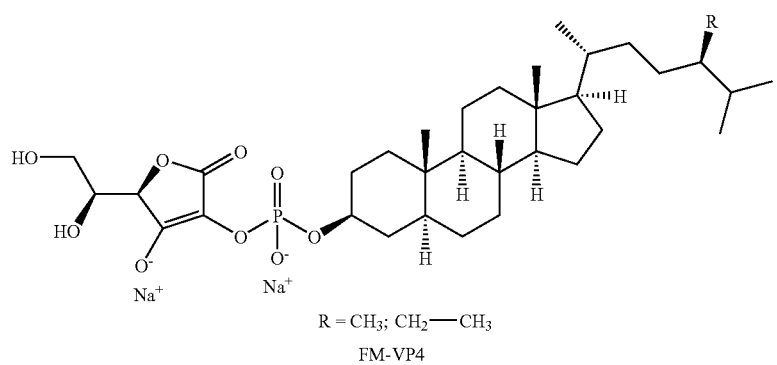

R = CH₃; CH₂—CH₃

FM-VP4

-continued
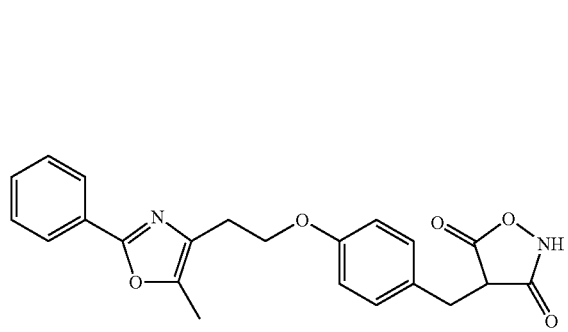
JTT-501
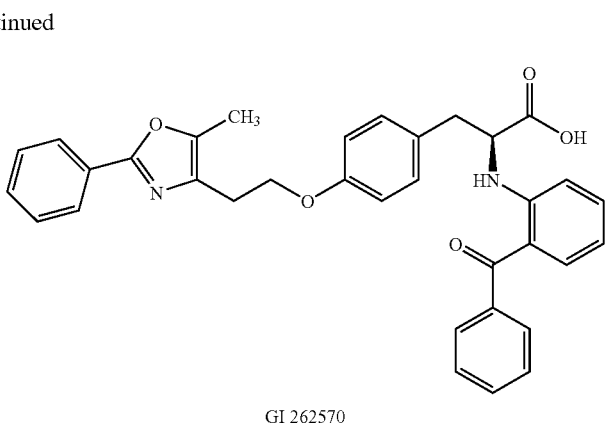
GI 262570
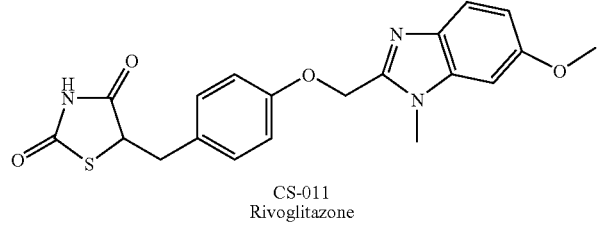
CS-011
Rivoglitazone
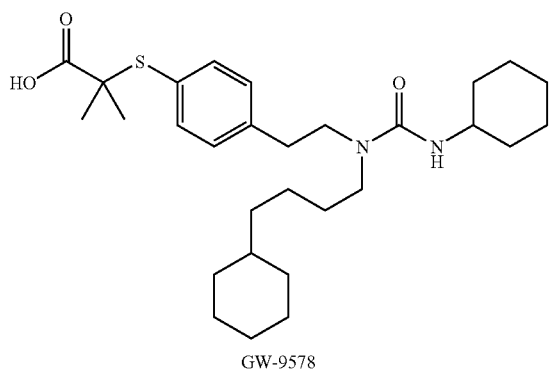
GW-9578
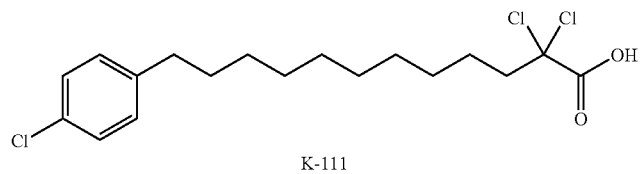
K-111
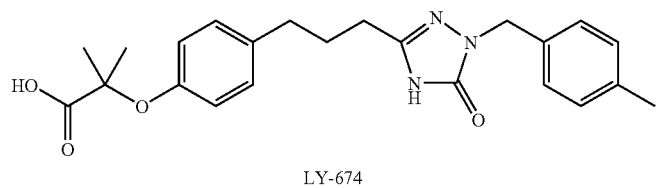
LY-674
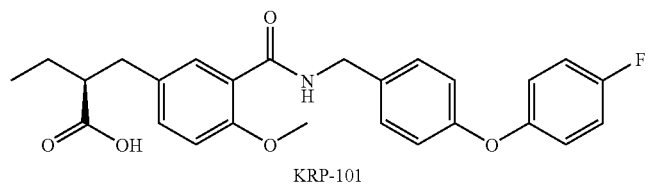
KRP-101
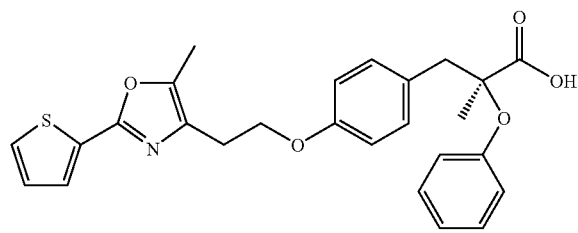
LY-510929

-continued
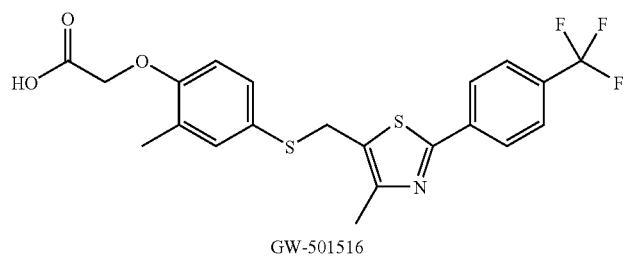
GW-501516
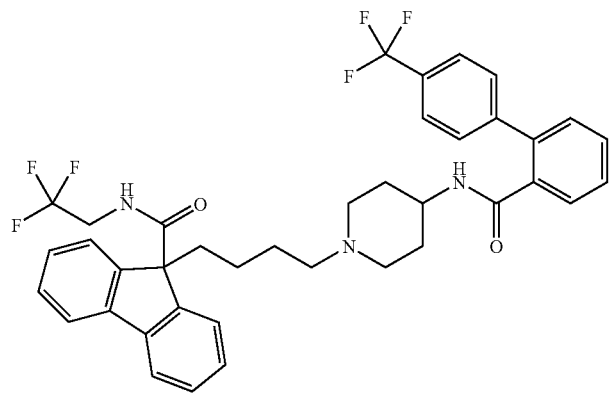
BMS-201038
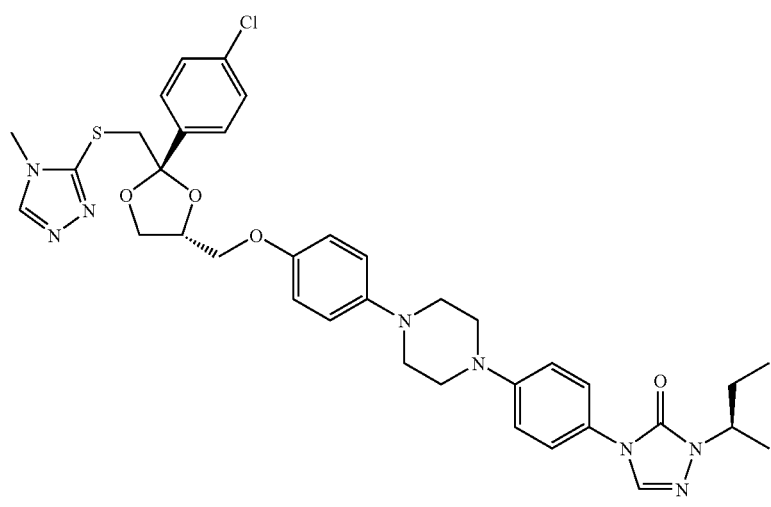
R-103757
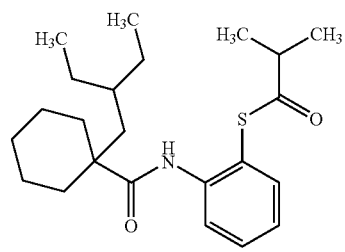
JTT-705
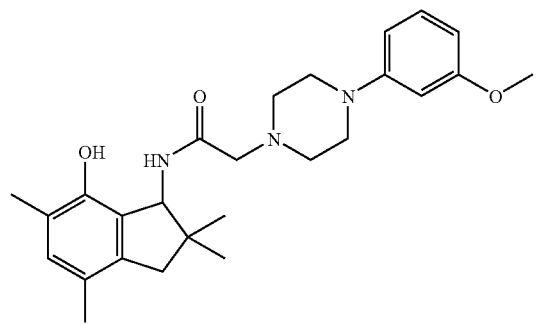
OPC-14117
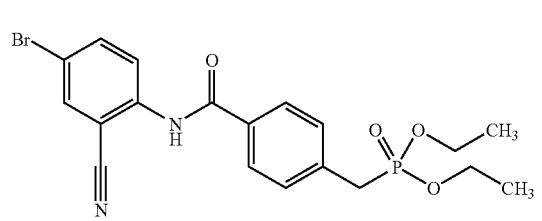
NO-1886

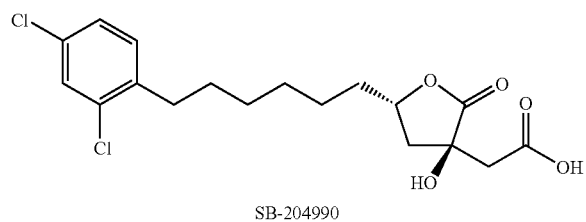
SB-204990
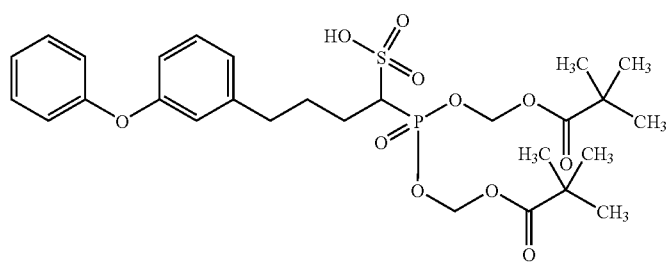
BMS-188494
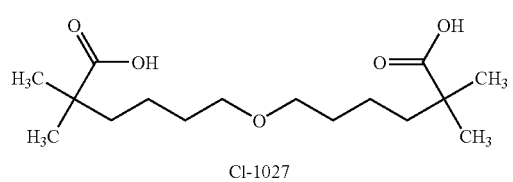
Cl-1027
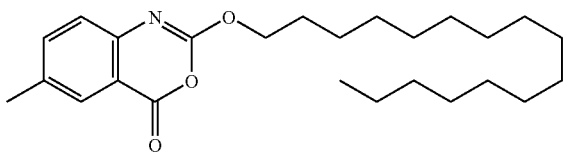
ATL-962
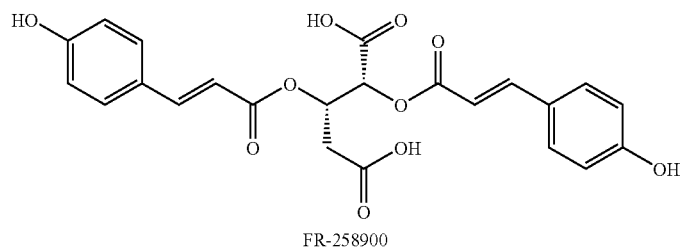
FR-258900
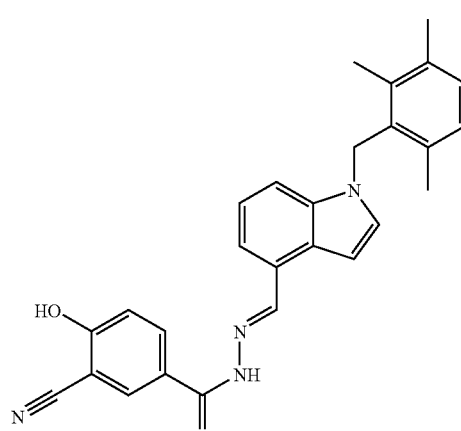
NNC-25-2504
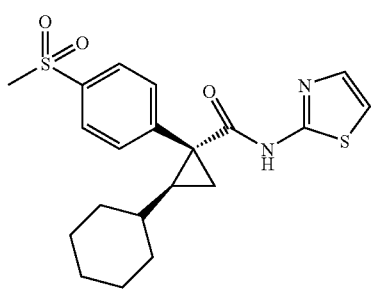
LY-2121260

-continued
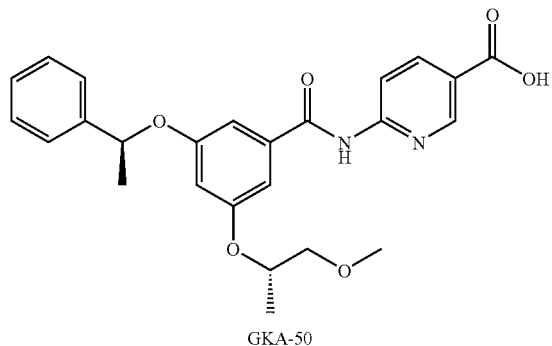
GKA-50
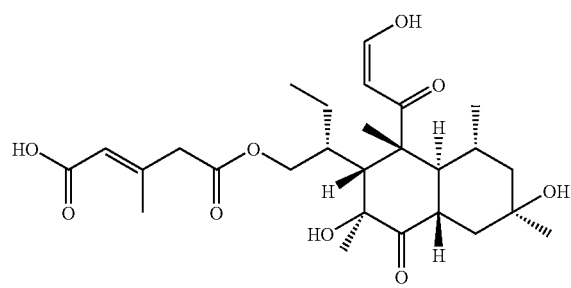
FR-225654
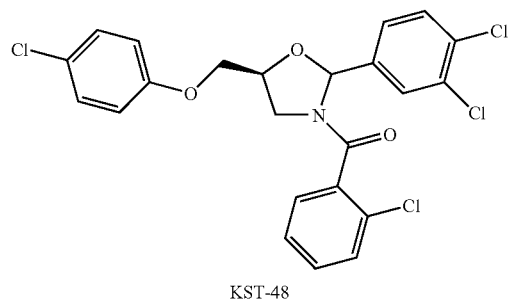
KST-48
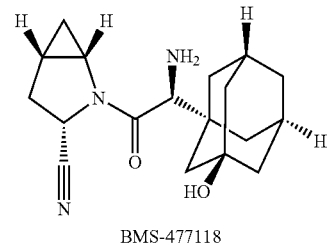
BMS-477118
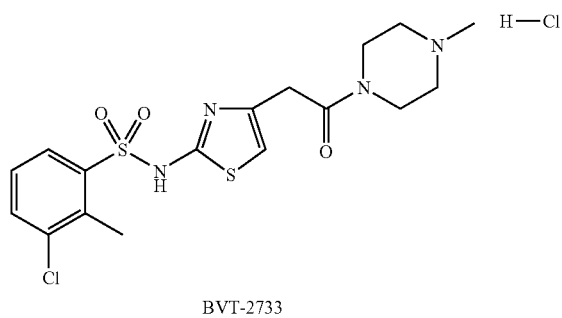
BVT-2733
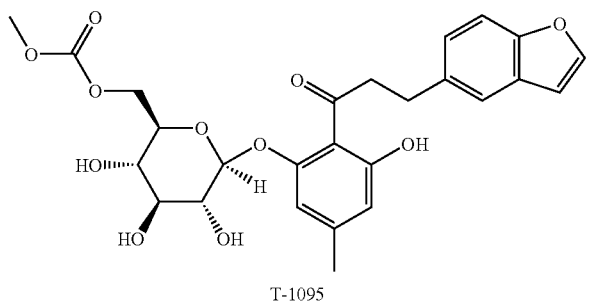
T-1095
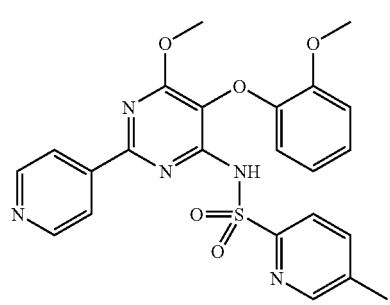
SPP-301
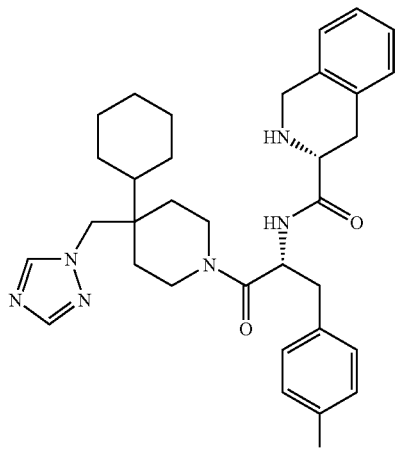
THIQ

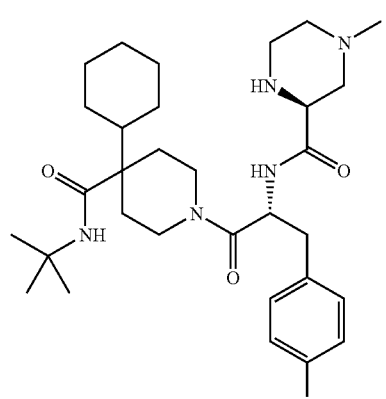
MB243
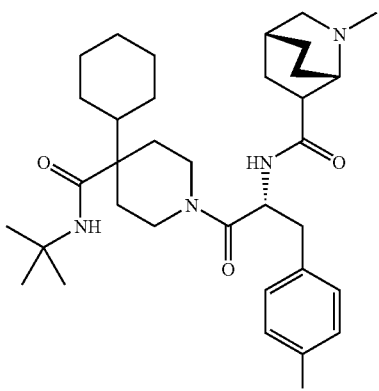
RY764
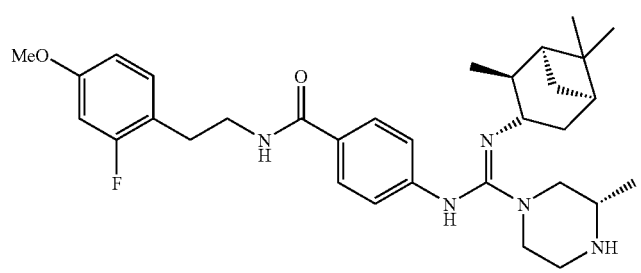
CHIR-785
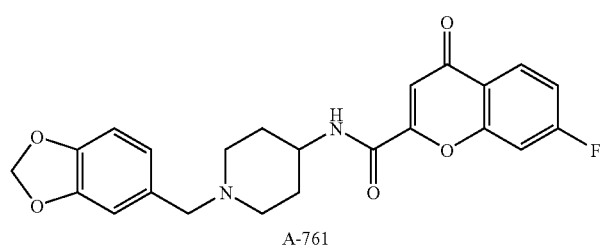
A-761
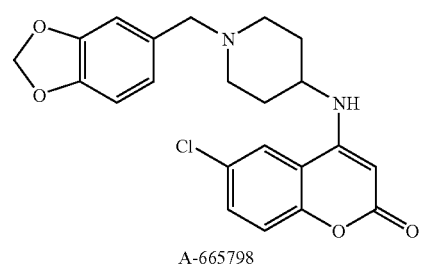
A-665798
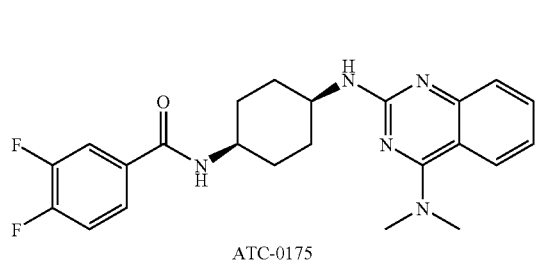
ATC-0175
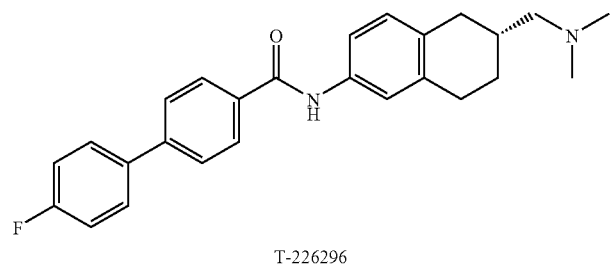
T-226296
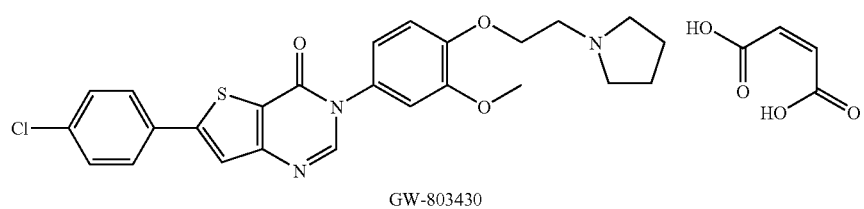
GW-803430

-continued

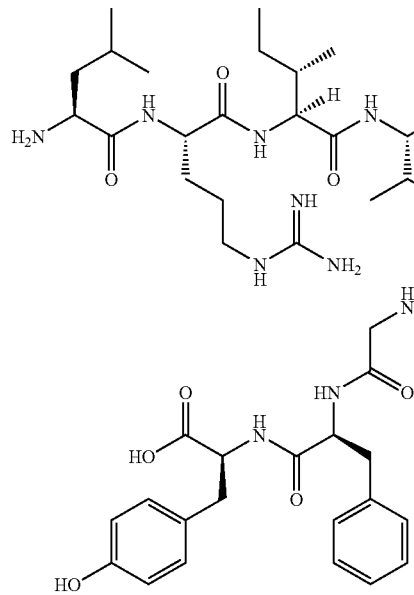
AOD-9604

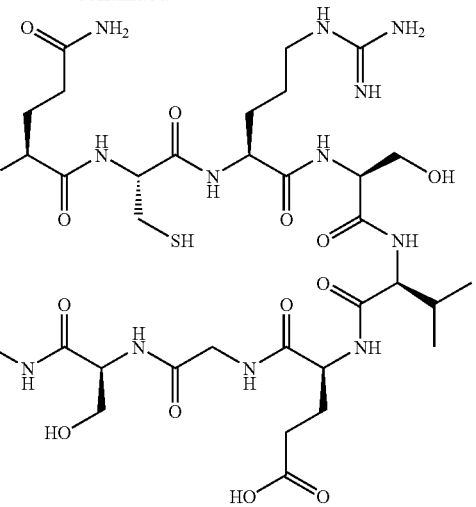
A-778193

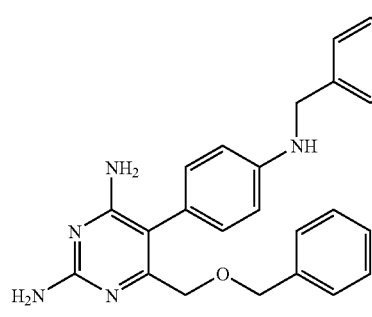

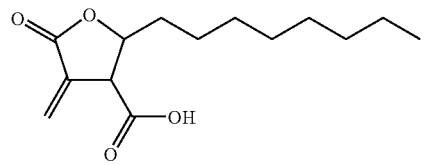
C75

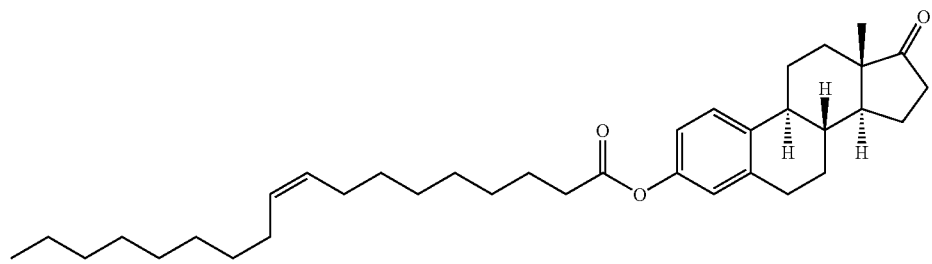
Oleoyl-estrone

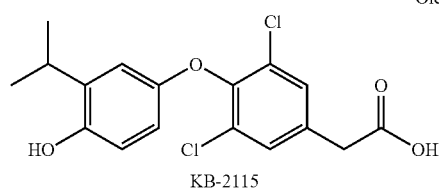
KB-2115

The activity of the compounds of the invention of the formula I was tested in the following enzyme test system:

EL Inhibition Assay:

EL is released as secretory protein in high concentration into cell culture medium (conditioned medium) by recombinant cell lines (CHO, HEK293). This is employed as enzyme solution after concentration.

EL Activity Assay

The phospholipase-specific substrate 1,2-bis(4,4-difluoro-5,7-dimethyl-4-bora-3a,4a-diaza-s-indacene-3-undecanoyl)-sn-glycero-3-phosphocholine, (manufacturer Molecular Probes) is used to characterize the enzymatic activity of endothelial lipase and the effect of inhibitors. Hydrolysis of the A1 ester linkage of this phospholipid by the enzyme liberates a fatty acid labeled with the fluorescent dye Bodipy which can be detected after separation by thin-layer chromatography on an HPTLC plate (silica gel 60, Merck) or directly in the reaction vessel by measuring the fluorescence. The substrate solution is prepared by dissolving 100 μg of 1,2-bis(4,4-difluoro-5,7-dimethyl-4-bora-3a,4a-diaza-s-indacene-3-undecanoyl)-sn-glycero-3-phospho-choline (manufacturer Molecular Probes) in 100 μl of DMSO and taking it up in 2.4 mg of tripalmitin (Sigma) in 393 μl of chloroform which contains 20 mg/ml of DOP-choline (1,2-dioleoyl-sn-glycero-3-phosphocholine). 39.3 μl of this lipid mixture are transferred into a fresh reaction vessel. After evaporation of the solvent, the lipid mixture is dissolved in 4 ml of 200 mM TRIS-HCl, 150 mM sodium chloride, pH=7.4, by sonication twice. The subsequent enzymic reaction takes place at 37° C. for 90 minutes. For this purpose, 20 μl of the substrate solution are incubated with 2 μl of inhibitor of appropriate concentration (dissolved in 10% DMSO, 10% strength DMSO solution is used as control) and 2 μl of enzyme solution (conditioned medium). Then 4 μl of the assay mixture are loaded onto an HPTLC plate (silica gel 60, Merck), and the liberated fluorescent dye is separated for detection with an eluent (diethyl ether:petroleum benzine:acetic acid [78:22:1]). After evaporation of the eluent, the plate is read in a fluorescence scanner. An increased release of the fluorescent dye in the uninhibited reaction is to be observed as a measure of the enzymic activity.

The enzymatic activity is reduced as a function of the inhibitor concentration used, and the inhibitor concentration at which a half-maximum enzymic activity is observed is called $IC_{50}$.

In these assays, the compounds of the examples showed the following $IC_{50}$ values:

| Example | $IC_{50}$ [μM] EL |
|---|---|
| 1 | 0.005 |
| 2 | 0.147 |
| 3 | 0.145 |
| 4 | 0.0005 |
| 5 | 0.008 |
| 6 | 0.143 |
| 7 | 0.083 |
| 8 | 0.047 |
| 9 | 0.037 |
| 21 | 0.059 |
| 23 | 0.044 |
| 24 | 0.039 |
| 28 | 0.059 |
| 29 | 0.143 |

Other Test Models

It is possible by means of various test models to test the suitability of the compounds of the invention as active pharmaceutical ingredient. Descriptions of such test models are given hereinafter by way of example.

Solubilities in Aqueous Systems

Adequate solubility of a substance in aqueous solvent systems is an important prerequisite for a (reproducible) pharmacological effect. Solubilities in aqueous systems can be determined by various methods. Suitable examples are solution precipitation methods ("kinetic solubility") and methods which investigate the dissolution of a solid sample until an equilibrium is set up ("thermodynamic solubility").

a) Kinetic solubility

A DMSO solution of the test compound (2.5 mM; 0.5 μL) is pipetted into 200 μL of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 μM using a nephelometer (e.g. Nephelostar Galaxy, BMG Labtech). The concentration of the test compound in the aqueous test solution is then raised to a theoretical 12.5 μM by adding further DMSO solution (2.5 mM; 0.5 μL), and the turbidity measurement is repeated. Further additions of DMSO solutions (1 μL, 2.5 mM; 0.5 μL, 10 mM; then 9×1 μL, 10 mM resulting in theoretical concentrations of 25 μM, 50 μM, 100 μM, 150 μM, 200 μM, 250 μM, 300 μM, 350 μM, 400 μM, 450 μM and 500 μM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values <6.25 μM, 6.25-500 μM and >500 μM.

Preferred compounds of the invention show a kinetic solubility in phosphate buffer (pH 7.4) of at least 12.5 μM; more preferably of at least 50 μM and even more preferably of at least 250 μM.

b) Thermodynamic Solubility

The integrated UV absorption from HPLC UV measurement of serial dilutions of the test compound in DMSO (500 μM, 100 μM, 50 μM, 10 μM and 1 μM) shows a linear correlation with the concentration in a calibration line. The test compound (500 μg) is shaken together with the aqueous test solution (250 μL) in a closed vessel (capacity: 1.5 mL) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration lines and stated as solubility of the test compound in the respective aqueous test solution.

Examples of aqueous test solutions are deionized water or aqueous phosphate buffer with various pH values (e.g. pH 1.2; pH 4.0; pH 6.8; pH 7.4; pH 9.0) which can be prepared from the commercial solution (phosphate buffered saline, 10×, Sigma) by dilution and adjustment with phosphoric acid or sodium hydroxide solution by standard methods.

Preferred compounds of the invention show a solubility in phosphate buffer (pH 7.4) of at least 12.5 μM; more preferably of at least 50 μM and even more preferably of at least 250 μM.

Metabolic Stability

The metabolic stability is determined by incubating the test compound (5 μm) with microsomal liver fractions (1 mg/ml protein with 0.1% w/v BSA; 1 mM NADPH, 0.5% DMSO) at 37° C. Analysis at an incubation time of 0 and 20 minutes takes place by means of LCMS/MS. Further descriptions of the test system and references on the experimental procedure are to be found in Plant, N.; Drug Discovery Today 2004, 9(7), 328-336 and Lau, Y. Y. et al.; Pharmaceutical Res. 2002, 19(11), 1606-1610.

Preparation Processes

The compounds of the invention of the formula I are prepared by methods known per se, e.g. by acylation of substituted or unsubstituted imidazolidine derivatives with carbamoyl chlorides III (method A), or in two stages by reacting imidazolidine derivatives II with phosgene or equivalents such as trichloromethyl chlorocarbonate, ditrichloromethyl carbonate or 4-nitrophenyl chloroformate and reacting the resulting imidazolidinecarboxylic acid derivative further with amines IV (method B). It is likewise possible also to react the imidazolidine derivatives II with the appropriate isocyanates V R1-N=C=O (method C).

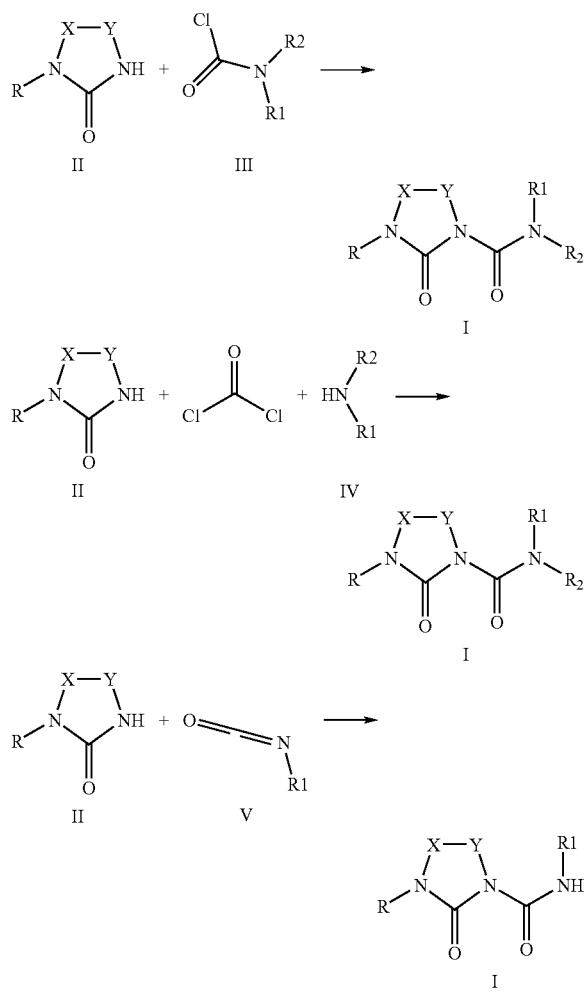

The radicals R (not equal to hydrogen) can also be introduced subsequently by alkylation of the compounds I (with R=hydrogen) by processes disclosed in the literature.

Radicals R of the type (C=O)—NR1aR2a can be introduced by methods A, B or C mentioned above. This can take place by employing components IVa (HNR1aR2a) and phosgene, or III or Va (O=C=NR1a) with a more than 2-fold excess compared with the starting compounds II.

The compounds of the formula I obtained by the processes described above can be separated by known separation methods such as, for example, by crystallization or chromatographic methods. It is possible in this way for example to separate monosubstituted from disubstituted imidazolidine derivatives.

Since acids are usually liberated in these reactions, it is advisable to add bases such as pyridine, triethylamine, sodium hydroxide solution or alkali metal carbonates as promoters. The reactions can be carried out in wide temperature ranges. It has usually proved advantageous to operate at from 0° C. to the boiling point of the solvent used. Examples of solvents employed are methylene chloride, THF, DMF, toluene, ethyl acetate, n-heptane, dioxane, diethyl ether or pyridine. Strong bases such as lithium hydride, sodium hydride or potassium tert-butoxide in aprotic solvents such as THF or DMF have also proved suitable when operating under anhydrous conditions.

The imidazolidine derivatives employed as starting compounds II are commercially available or can be prepared by processes disclosed in the literature (A. Boeijen; J. W: A. Kruijtzer, R. M. J. Liskamp, Bioorg. Med. Chem. Lett. 1998 (8), 2375-2380; J. C. Hodges, S. Klutchko, U.S. Pat. No. 5,308,853).

The examples detailed below serve to illustrate the invention without, however, restricting it.

The identity of the compounds was checked by mass spectrometry.

EXAMPLES

Example 1

3-Benzyl-2,5-dioxoimidazolidine-1-hexylcarboxamide

1-Benzylimidazolidine-2,4-dione (100 mg, 0.526 mmol) and 1-isocyanatohexane (80.3 mg, 0.63 mmol) and, if required, a catalytic amount of 4-dimethylaminopyridine were dissolved in 10 ml of toluene and 0.5 ml of pyridine and stirred at 115° C. for 6 h. Then a further 80 mg of 1-isocyanatohexane were added, and the mixture was stirred at 115° C. for a further 6 h. The reaction mixture was concentrated and the residue was taken up in ethyl acetate and H2O, and the org. phases were washed twice with water, concentrated and purified by preparative HPLC (PR18, acetonitrile/water 0.1% TFA). Yield: 11.3 mg (7%), M+H+:318.14.

Example 2

3-Benzyl-2,5-dioxoimidazolidine-1-(2-methylbenzyl)carboxamide

1-Benzylimidazolidine-2,4-dione (100 mg, 0.526 mmol) and 1-isocyanatomethyl-2-methylbenzene (92.9 mg, 0.63 mmol) were reacted in analogy to example 1. Yield: 54 mg (30%), M+H+:338.17.

Example 3

3-Benzyl-2,5-dioxoimidazolidine-1-((S)-indan-1-yl)carboxamide

1-Benzylimidazolidine-2,4-dione (100 mg, 0.526 mmol) and (S)-1-isocyanatoindane (100.4 mg, 0.63 mmol) were reacted in analogy to example 1. Yield: 95 mg (52%), M+H+: 350.19.

Example 4

3-Benzyl-2,5-dioxoimidazolidine-1-((R)-indan-1-yl)carboxamide

1-Benzylimidazolidine-2,4-dione (100 mg, 0.526 mmol) and (R)-1-isocyanatoindane (100.4 mg, 0.63 mmol) were reacted in analogy to example 1. Yield: 48 mg (26%), M+H+: 350.19.

Example 5

3-Benzyl-2,5-dioxoimidazolidine-1-(1,2,3,4-tetrahydronaphthalen-1-yl)carboxamide 1-Benzylimidazolidine-2,4-dione (100 mg, 0.526 mmol) and 1-isocyanato-1,2,3,4-tetrahydronaphthalene (109.3 mg, 0.63 mmol) were reacted in analogy to example 1. Yield: 60 mg (31%), M+H+: 364.16.

Example 6

3-Benzyl-2,5-dioxoimidazolidine-1-(2-thiophen-2-ylethyl)carboxamide

1-Benzylimidazolidine-2,4-dione (100 mg, 0.526 mmol) and 2-(2-isocyanato-ethyl)thiophene (96.7 mg, 0.63 mmol) were reacted in analogy to example 1. Yield: 53.5 mg (30%), M+H+: 344.08.

Example 7

3-Benzyl-2,5-dioxoimidazolidine-1-heptylcarboxamide

1-Benzylimidazolidine-2,4-dione (100 mg, 0.526 mmol) and 1-isocyanatoheptane (89.1 mg, 0.63 mmol) were reacted in analogy to example 1. Yield: 63.8 mg (37%), M+H+: 332.20.

Example 8

3-Methyl-2,5-dioxoimidazolidine-1-hexyl carboxamide

1-Methylimidazolidine-2,4-dione (100 mg, 0.876 mmol) and 1-isocyanatohexane (133.8 mg, 1.05 mmol) were reacted in analogy to example 1. Yield: 43.2 mg (20%), M+H+: 242.15.

Example 9

3,4,4-Trimethyl-2,5-dioxoimidazolidine-1-hexylcarboxamide 1,5,5-Trimethylimidazolidine-2,4-dione (100 mg, 0.70 mmol) and 1-isocyanatohexane (107.4 mg, 0.84 mmol) were reacted in analogy to example 1. Yield: 31.5 mg (17%), M+H+: 270.17.

Example 10

3-Benzyl-2,4-dioxoimidazolidine-1-hexylcarboxamide

3-Benzylimidazolidine-2,4-dione (100 mg, 0.526 mmol) and 1-isocyanatohexane (80.2 mg, 0.63 mmol) were reacted in analogy to example 1. Yield: 19.3 mg (12%), M+H+: 318.15.

Example 11

3-Benzyl-2,4-dioxoimidazolidine-1-(2-methylbenzyl)carboxamide

3-Benzylimidazolidine-2,4-dione (100 mg, 0.526 mmol) and 1-isocyanatomethyl-2-methylbenzene (92.9 mg, 0.63 mmol) were reacted in analogy to example 1. Yield: 75.3 mg (42%), M+H+: 338.14.

Example 12

3-Benzyl-2,4-dioxoimidazolidine-1-heptylcarboxamide

3-Benzylimidazolidine-2,4-dione (100 mg, 0.526 mmol) and 1-isocyanatoheptane (89.1 mg, 0.63 mmol) were reacted in analogy to example 1. Yield: 48 mg (28%), M+H+: 332.17.

Example 13

3-Benzyl-2,4-dioxoimidazolidine-1-(2-thiophen-2-ylethyl)carboxamide

3-Benzylimidazolidine-2,4-dione (100 mg, 0.526 mmol) and 2-(2-isocyanato-ethyl)thiophene (96.7 mg, 0.63 mmol) were reacted in analogy to example 1. Yield: 34.5 mg (19%), M+H+:

Example 14

5,5-Dimethyl-2,4-dioxoimidazolidine-1-hexylcarboxamide 5,5-Dimethyl-3-morpholin-4-ylmethylimidazolidine-2,4-dione (100 mg, 0.44 mmol) and 1-isocyanatohexane (56 mg, 0.44 mmol) were reacted in analogy to example 1. Yield: 8 mg (7%), M+H+: 256.21.

Example 15

3-(5,5-Dimethyl-2-oxotetrahydrofuran-3-yl)-5,5-dimethyl-2,4-dioxoimidazolidine-1-hexylcarboxamide 3-(5,5-Dimethyl-2-oxotetrahydrofuran-3-yl)-5,5-dimethylimidazolidine-2,4-dione (100 mg, 0.416 mmol) and 1-isocyanatohexane (52.9 mg, 0.416 mmol) were reacted in analogy to example 1. Yield: 6 mg (4%), M+H+: 368.25.

Example 16

3-Benzyl-2,5-dioxoimidazolidine-1-pentylcarboxamide

1-Benzylimidazolidine-2,4-dione (100 mg, 0.526 mmol) and 1-isocyanatopentane (71.4 mg, 0.63 mmol) were reacted in analogy to example 1. Yield: 15 mg (9%), M+H+: 304.18.

Example 17

3-Benzyl-2,5-dioxoimidazolidine-1-cyclohexylcarboxamide

1-Benzylimidazolidine-2,4-dione (100 mg, 0.526 mmol) and isocyanatocyclohexane (79 mg, 0.63 mmol) were reacted in analogy to example 1. Yield: 22 mg (13%), M+H+: 316.18.

Example 18

3-Benzyl-2,5-dioxoimidazolidine-1-cyclohexylmethylcarboxamide

1-Benzylimidazolidine-2,4-dione (100 mg, 0.526 mmol) and isocyanatomethylcyclohexane (87.8 mg, 0.63 mmol) were reacted in analogy to example 1. Yield: 36.8 mg (21%), M+H+: 330.18.

Example 19

3-Benzyl-2,5-dioxoimidazolidine-1-benzylcarboxamide

1-Benzylimidazolidine-2,4-dione (100 mg, 0.526 mmol) and isocyanatomethyl-benzene (84 mg, 0.63 mmol) were reacted in analogy to example 1. Yield: 39.8 mg (23%), M+H+: 324.14.

Example 20

3-Butyl-2,5-dioxoimidazolidine-1-hexylcarboxamide

1-Butylimidazolidine-2,4-dione (100 mg, 0.64 mmol) and 1-isocyanatohexane (97.7 mg, 0.768 mmol) were reacted in DMF in analogy to example 1. Yield: 9 mg (5%), M+H+: 284.50.

Example 21

3-Butyl-2,5-dioxoimidazolidine-1-heptylcarboxamide

1-Butylimidazolidine-2,4-dione (100 mg, 0.64 mmol) and 1-isocyanatoheptane (108.5 mg, 0.768 mmol) were reacted in DMF in analogy to example 1. Yield: 15 mg (8%), M+H+: 298.18.

Example 22

3-Butyl-2,5-dioxoimidazolidine-1-(1,2,3,4-tetrahydronaphthalen-1-yl)carboxamide

1-Butylimidazolidine-2,4-dione (100 mg, 0.64 mmol) and 1-isocyanato-1,2,3,4-tetra-hydronaphthalene (133 mg, 0.768 mmol) were reacted in DMF in analogy to example 1. Yield: 24.3 mg (12%), M+H+: 330.17.

Example 23

1,3-Dioxohexahydroimidazo[1,5-a]pyridine-2-hexylcarboxamide a) Tetrahydroimidazo[1,5-a]pyridine-1,3-dione Methyl pipecolinecarboxylate hydrochloride (1 g, 5.567 mmol) was dissolved in water and, at room temperature, potassium cyanate (452 mg, 5.567 mmol) in 2 ml of water was added dropwise. After stirring at room temperature for 1 h, potassium cyanate (130 mg) in 2 ml of water was again added dropwise, and stirring was continued for 3 h. The reaction solution was acidified with hydrochloric acid, concentrated and stirred with a little water. The solid was filtered off with suction and dried. Yield: 191 mg (22%), M+H+: 155.10. Further product could be isolated on repeating the workup.

b) 1,3-Dioxohexahydroimidazo[1,5-a]pyridine-2-hexylcarboxamide

Tetrahydroimidazo[1,5-a]pyridine-1,3-dione (690 mg, 4.476 mmol) and isocyanato-hexane (1.5 ml, 10.3 mmol, addition in several portions) were stirred in 30 ml of dioxane at 80° C. for 3 h and at 110° C. for 5 h. Concentration was followed by purification by preparative HPLC (PR18, acetonitrile/water 0.1% TFA). Yield: 23 mg (2%), M+H+:282.20.

Example 24

1,3-Dioxo-1,5,10,10a-tetrahydroimidazo[1,5-b]isoquinoline-2-hexylcarboxamide 10,10a-Dihydro-5H-imidazo[1,5-b]isoquinoline-1,3-dione was prepared from ethyl 1,2,3,4-tetrahydroisoquinoline-3-carboxylate in analogy to example 23 (yield: 85%) and then 1.48 mmol were reacted as described in example 23 with isocyanatohexane. Yield: 61 mg (12%), M+H+:330.20.

Example 25

1,3-Dioxohexahydroimidazo[1,5-a]pyridine-2-(2-methylbenzyl)carboxamide

Tetrahydroimidazo[1,5-a]pyridine-1,3-dione was reacted with 1-isocyanatomethyl-2-methylbenzene in analogy to example 23. Yield: 12%, M+H+:302.23.

Example 26

1,3-Dioxo-1,5,10,10a-tetrahydroimidazo[1,5-b]isoquinoline-2-((S)-indan-1-yl)carboxamide 10,10a-Dihydro-5H-imidazo[1,5-b]isoquinoline-1,3-dione was reacted with (S)-1-isocyanatoindane in analogy to example 23. Yield: 5%, M+H+: 362.11.

Example 27

1,3-Dioxo-1,5,10,10a-tetrahydroimidazo[1,5-b]isoquinoline-2-((R)-indan-1-yl)carboxamide 10,10a-Dihydro-5H-imidazo[1,5-b]isoquinoline-1,3-dione was reacted with (R)-1-isocyanatoindane in analogy to example 23. Yield: 6%, M+H+: 362.13.

Example 28

1,3-Dioxo-1,5,10,10a-tetrahydroimidazo[1,5-b]isoquinoline-2-(1,2,3,4-tetra-hydronaphthalen-1-yl)carboxamide 10,10a-Dihydro-5H-imidazo[1,5-b]isoquinoline-1,3-dione was reacted with 1-isocyanato-1,2,3,4-tetrahydronaphthalene in analogy to example 23. Yield: 8%, M+H+: 376.12.

Example 29

1,3-Dioxo-1,5,10,10a-tetrahydroimidazo[1,5-b]isoquinoline-2-methylbenzyl-2-carboxamide 10,10a-Dihydro-5H-imidazo[1,5-b]isoquinoline-1,3-dione was reacted with 1-isocyanatomethyl-2-methylbenzene in analogy to example 23. Yield: 2%, M+H+: 350.12.

Example 30

1,3-Dioxohexahydroimidazo[1,5-a]pyridine-2-((S)-1,2,3,4-tetrahydronaphthalen-1-yl)carboxamide Tetrahydroimidazo[1,5-a]pyridine-1,3-dione was reacted with (S)-1-isocyanato-1,2,3,4-tetrahydronaphthalene in analogy to example 23. Yield: 24%, M+H+:328.16.

Example 31

1,3-Dioxohexahydroimidazo[1,5-a]pyridine-2-((S)-indan-1-yl)carboxamide

Tetrahydroimidazo[1,5-a]pyridine-1,3-dione was reacted with (S)-1-isocyanatoindane in analogy to example 23. Yield: 9%, M+H+: 314.14.

Example 32

1,3-Dioxohexahydroimidazo[1,5-a]pyridine-2-((R)-indan-1-yl)carboxamide

Tetrahydroimidazo[1,5-a]pyridine-1,3-dione was reacted with (R)-1-isocyanatoindane in analogy to example 23. Yield: 18%, M+H+:314.14.

We claim:

1. A compound of formula I

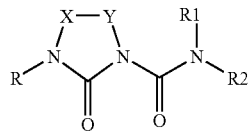

wherein:

X and Y are independently —C(R3)(R4)-, —(C═O)—, or —(C═S), provided that at least one of X and Y is —(C═O)— or —(C═S)—, and X and Y cannot both simultaneously be —(C═O)— or —(C═S)—, or X and Y together are C(R3)═C(R3);

R is —(C═O)—NR1aR2a, —(C═O)—O—R1b, ($C_1$-$C_5$)-haloalkyl, (CR5R6)$_m$-O(R7), ($C_1$-$C_3$)-alkyloxy-($C_1$-$C_3$)-alkylene, aryl, heterocycle, ($C_1$-$C_4$)-alkylene-aryl, ($C_1$-$C_4$)-alkylene-heteroaryl, or ($C_1$-$C_4$)-alkylene-($C_5$-$C_{12}$)-cycloalkyl, wherein the cycloalkyl, aryl, heterocycle or heteroaryl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy—($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_8$)-alkynyl, ($C_0$-$C_8$)-alkylene-aryl, O—($C_0$-$C_8$)-alkylene-aryl, S-aryl, ($C_0$-$C_8$)-alkylene-heteroaryl, N(R5)(R6), $SO_2$—$CH_3$, $SO_2$—$NH_2$, $SF_5$, COOH, COO—($C_1$-$C_6$)-alkyl, CON(R5)(R6), N(R5)CO(R6), N(R5)$SO_2$(R6), CO(R5), (CR5R6)$_m$-O(R7), O—CO—N(R5)(R6), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R5)(R6), wherein the aryl or heteroaryl may in turn be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R8)(R9), $SO_2$—$CH_3$, $SF_5$, COOH, COO—($C_1$-$C_6$)-alkyl, CON(R8)(R9), N(R8)CO(R9), N(R8)$SO_2$(R9), CO(R8), (CR8R9)$_m$''-O(R10), O—CO—N(R8)(R9), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R8)(R9); or R and X when X is —C(R3)(R4)-, together with the nitrogen atom to which they are attached form a monocyclic, saturated or partly unsaturated 4- to 7-membered ring system or a bicyclic saturated or partly unsaturated 8- to 14-membered ring system whose individual members of the ring systems may be replaced by one to three atoms or atomic groups selected from —CHR11-, —CR11R12-, —(C═R11)-, ═C(R11)-, —NR11-, —C(═O)-, —O—, —S—, —SO—, and —$SO_2$-, provided that two units from the series —O—, —S—, —SO—, and —$SO_2$— may not be adjacent;

m, m' and m" are independently 0, 1, 2, 3, 4, 5, or 6;

R5, R6, R7, R8, R9 and R10 are independently hydrogen or ($C_1$-$C_8$)-alkyl;

R11 and R12 are independently hydrogen, ($C_1$-$C_6$)-alkyl, aryl, ($C_3$-$C_{12}$)-cycloalkyl, ($C_1$-$C_4$)-alkylene-aryl, or ($C_1$-$C_3$)-alkylene-($C_3$-$C_{12}$)-cycloalkyl, wherein the aryl or cycloalkyl may be substituted by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_2$-$C_6$)-alkynyl, N(R13)(R14), $SO_2$—$CH_3$, $SO_2$—$NH_2$, $SF_5$, COOH, COO—($C_1$-$C_6$)-alkyl, CON(R13)(R14), N(R13)CO(R14), N(R13)$SO_2$(R14), CO(R13), (CR13R14)$_n$-O(R15), O—CO—N(R13)(R14), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R13)(R14);

n is 0, 1, 2, 3, 4, 5, or 6;

R13, R14 and R15 are independently hydrogen or ($C_1$-$C_8$)-alkyl;

R1, R1a and R1b are independently ($C_5$-$C_{16}$)-alkyl, $CH_2$-aryl, ($C_1$-$C_2$)-alkylene-heteroaryl, or $CH_2$—($C_5$-$C_{12}$)-cycloalkyl, wherein the aryl, heteroaryl or cycloalkyl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, ($C_0$-$C_8$)-alkylene-aryl, O—($C_0$-$C_8$)-alkylene-aryl, S-aryl, ($C_0$-$C_8$)-alkylene-heteroaryl, N(R16)(R17), $SO_2$—$CH_3$, $SO_2$—$NH_2$, $SF_5$, COOH, CCO—($C_1$-$C_6$)-alkyl, CON(R16)(R17), N(R16)CO(R17), N(R16)$SO_2$(R17), CO(R16), (CR16R17)$_0$-O(R18), O—CO—N(R16)(R17), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R16)(R17), wherein the aryl or heteroaryl in turn may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R19)(R20), $SO_2$—$CH_3$, $SF_5$, COOH, COO—($C_1$-$C_6$)-alkyl, CON(R19)(R20), N(R19)CO(R20), N(R19)$SO_2$(R20), CO(R19), (CR19R20)$_0$-O(R21), O—CO—N(R19)(R20), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R19)(R20);

o and o' are independently 0, 1, 2, 3, 4, 5, or 6;

R16, R17, R18, R19, R20 and R21 are independently hydrogen or ($C_1$-$C_8$)-alkyl; or R1, R1a and R1b may independently be a radical of formula Ia

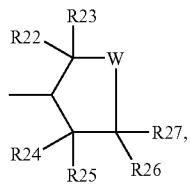

wherein:
- W is —C(R28)(R29)-, —C(R28)(R29)—C(R28a)(R29a)-, or —C(R28)(R29)—O—;
- R22, R23, R24, R25, R26, R27, R28, R29, R28a, R29a are independently hydrogen, F, Cl, Br, I, OH, $CF_3$, $NO_2$, CN, $OCF_3$, $SF_5$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, N(R30)(R31), $SO_2$—$CH_3$, COOH, COO—($C_1$-$C_6$)-alkyl, CON(R30)(R31), N(R30)CO(R31), N(R30)$SO_2$(R31), CO(R30), (CR30R31)$_p$-O(R32), O—CO—N(R30)(R31), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R30)(R31); or
- R22 and R28 or R23 and R29 together with the carbon atoms to which they are attached form a monocyclic, 5 or 6 membered saturated, partly unsaturated or aromatic ring system whose individual members may be replaced by —CHR33-, —CR33R34-, or =(C—R33)-; or R24 and R26, or R25 and R27 together with the carbon atoms to which they are attached form a monocyclic, 5 or 6 membered saturated, partly unsaturated or an aromatic ring system whose individual members may be replaced by —CHR33-, —CR33R34-, or =(C—R33)-;
- p is 0, 1, 2, 3, 4, 5, or 6;
- R30, R31 and R32 are independently hydrogen or ($C_1$-$C_6$)-alkyl;
- R33 and R34 are independently F, Cl, Br, I, OH, $CF_3$, $NO_2$, CN, $OCF_3$, $SF_5$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R35)(R36), $SO_2$—$CH_3$, COOH, COO—($C_1$-$C_6$)-alkyl, CON(R35)(R36), N(R35)CO(R36), N(R35)$SO_2$(R36), CO(R35), (CR35R36)$_q$-O(R37), O—CO—N(R35)(R36), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R35)(R36);
- q is 0, 1, 2, 3, 4, 5, or 6;
- R35, R36 and R37 are independently hydrogen or ($C_1$-$C_6$)-alkyl;
- R2 and R2a are independently hydrogen or ($C_1$-$C_8$-alkyl; and
- R3 and R4 are independently hydrogen, ($C_1$-$C_6$)-alkyl, or benzyl;
- or a tautomeric form or a physiologically tolerated salt thereof;
- provided that R1 is not pentyl, $CH_2$-phenyl, —$CH_2$-(2-Cl-phenyl), cyclohexyl, or -(2-methylcyclohexyl) when X is $CH_2$, Y is CO, R is methyl and R2 is H.

2. The compound according to claim 1, wherein R2 is hydrogen, or a tautomeric form or a physiologically tolerated salt thereof.

3. The compound according to claim 1, wherein
Y is —(C=O)—; and
X is —C(R3)(R4)-;
or
X is —(C=O)—; and
Y is —C(R3)(R4)-;
R is —(C=O)—NR1aR2a, —(C=O)—O—R1b, ($C_1$-$C_3$)-haloalkyl, (CR5R6)$_m$-O(R7), phenyl, heterocycle, ($C_1$-$C_4$)-alkylene-phenyl, ($C_1$-$C_4$)-alkylene-heteroaryl, or ($C_1$-$C_4$)-alkylene-($C_5$-$C_{12}$)-cycloalkyl, wherein the cycloalkyl, phenyl, heterocycle or heteroaryl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, ($C_0$-$C_8$)-alkylene-aryl, O—($C_0$-$C_8$)-alkylene-aryl, S-aryl, ($C_0$-$C_8$)-alkylene-heteroaryl, N(R5)(R6), $SO_2$—$CH_3$, $SO_2$—$NH_2$, $SF_5$, COOH, COO—($C_1$-$C_6$)-alkyl, CON(R5)(R6), N(R5)CO(R6), N(R5)$SO_2$(R6), CO(R5), (CR5R6)$_m$-O(R7), O—CO—N(R5)(R6), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R5)(R6), where the aryl or heteroaryl may in turn be substituted one or more times by
F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R8)(R9), $SO_2$—$CH_3$, $SF_5$, COOH, CCO—($C_1$-$C_6$)-alkyl, CON(R8)(R9), N(R8)CO(R9), N(R8)$SO_2$(R9), CO(R8), (CR8R9)$_m$-O(R10), O—CO—N(R8)(R9), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene -CO—N(R8)(R9); or
R and X when X is —C(R3)(R4)-, together with the nitrogen atom to which they are attached form a monocyclic, saturated 5- to 7-membered ring system or a bicyclic partly unsaturated 8- to 14 membered ring system whose individual members may be replaced by one to three atoms or atomic groups selected from —CHR11-, —CR11R12-, —(C=R11)-, —NR11-, —C(=O)—, and —O—, provided that two units of —O—may not be adjacent;
R11 and R12 are independently hydrogen, ($C_1$-$C_6$)-alkyl, phenyl, ($C_3$-$C_{12}$)-cycloalkyl, ($C_1$-$C_4$)-alkylene-phenyl, or ($C_1$-$C_3$)-alkylene—($C_3$-$C_{12}$)-cycloalkyl, wherein the phenyl or cycloalkyl may be substituted by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_2$-$C_6$)-alkynyl, N(R13)(R14), $SO_2$—$CH_3$, $SO_2$—$NH_2$, $SF_5$, COOH, CCO—($C_1$-$C_6$)-alkyl, CON(R13)(R14), N(R13)CO(R14), N(R13)$SO_2$(R14), CO(R13), (CR13R14)$_n$-O(R15), O—CO—N(R13)(R14), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R13)(R14); and
R1, R1a and R1b are independently ($C_5$-$C_{12}$)-alkyl, —$CH_2$-phenyl, ($C_1$-$C_2$)-alkylene-heteroaryl, —$CH_2$—($C_5$-$C_{12}$)-cycloalkyl, or ($C_5$-$C_6$)-cycloalkyl, wherein the phenyl, heteroaryl or cycloalkyl may be substituted one or more times by F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, ($C_0$-$C_8$)-alkylene-phenyl, O—($C_0$-$C_8$)-alkylene-phenyl, S-phenyl, ($C_0$-$C_8$)-alkylene-heteroaryl, N(R16)(R17), $SO_2$—$CH_3$, $SO_2$—$NH_2$, $SF_5$, COOH, CCO—($C_1$-$C_6$)-alkyl, CON(R16)(R17), N(R16)CO(R17), N(R16)$SO_2$(R17), CO(R16), (CR16R17)$_o$-O(R18), O—CO—N(R16)(R17), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R16)(R17), wherein the phenyl or heteroaryl may in turn be substituted one or more times by F, Cl, Br, I, OH, $CF_3$, $NO_2$, CN, $OCF_3$, O—($C_1$-$C_6$)-alkyl, O—($C_1$-$C_4$)-alkoxy—($C_1$-$C_4$)-alkyl, S—($C_1$-$C_6$)-alkyl, ($C_1$-$C_6$)-alkyl, ($C_2$-$C_6$)-alkenyl, ($C_2$-$C_6$)-alkynyl, N(R19)(R20), $SO_2$—$CH_3$, $SF_5$, COOH, COO—($C_1$-$C_6$)-alkyl, CON(R19)(R20), N(R19)CO(R20), N(R19)$SO_2$(R20), CO(R19), (CR19R20)$_o'$—O(R21), O—CO—N(R19)(R20), O—CO—($C_1$-$C_6$)-alkylene-CO—O—($C_1$-$C_6$)-alkyl, O—CO—($C_1$-$C_6$)-alkylene-CO—OH, or O—CO—($C_1$-$C_6$)-alkylene-CO—N(R19)(R20); or R1, R1a and R1b may independently be a radical of formula Ib or a tautomeric form or a physiologically tolerated salt thereof.

4. The compound according to claim 1, wherein:
Y is —(C=O)—; and
X is —C(R3)(R4)-; or
X is —(C=O)—; and
Y is —C(R3(R4)-;
R is (CR5R6)$_m$-O(R7), phenyl, or —$CH_2$-phenyl, wherein the phenyl may be substituted once or twice by F, Cl, Br, $CF_3$, O—($C_1$-$C_6$)-alkyl, ($C_1$-$C_6$)-alkyl, O—($C_2$-$C_4$)-haloalkyl, N(R5)(R6), $SO_2$—$CH_3$, $SO_2$—$NH_2$, COOH, COO—($C_1$-$C_6$)-alkyl, CON(R5)(R6), CO(R5), or (CR5R6)$_m'$—O(R7); or
R and X when X is —C(R3)(R4)-, together with the nitrogen atom to which they are attached form a monocyclic, saturated 6-membered ring system or a bicyclic partly unsaturated 9- to 11-membered ring system whose individual members may be replaced by one to two atoms or atomic groups selected from —CHR11-, —CR11R12-, —(C=R11)-, and =C(R11)-;
m and m' are independently 0, 1, 2, or 3;
R11 and R12 are independently hydrogen or ($C_1$-$C_6$)-alkyl;
R1 is ($C_5$-$C_8$)-alkyl, —$CH_2$-phenyl, or ($C_1$-$C_2$)-alkylene-heteroaryl, —$CH_2$—($C_5$-$C_7$)-cycloalkyl, or ($C_5$-$C_6$)-cycloalkyl, wherein the heteroaryl is thiophene, benzothiophene, pyridine, or pyrazole, and wherein the phenyl, heteroaryl or cycloalkyl may be substituted one or more times by F, Cl, Br, OH, $CF_3$, $NO_2$, CN, $OCF_3$, O—($C_1$-$C_6$)-alkyl, ($C_1$-$C_6$)-alkyl, ($C_0$-$C_8$)-alkylene-phenyl, O—($C_0$-$C_8$)-alkylene-phenyl, ($C_0$-$C_8$)-alkylene-heteroaryl, N(R16)(R17), $SO_2$—$CH_3$, $SO_2$—$NH_2$, COOH, COO—($C_1$-$C_6$)-alkyl, CON(R16)(R17), CO(R16), or (CR16R17)$_o$-O(R18), wherein the phenyl or heteroaryl may in turn be substituted one or more times by F, Cl, Br, OH, $CF_3$, $NO_2$, CN, $OCF_3$, O—($C_1$-$C_6$)-alkyl, ($C_1$-$C_6$)-alkyl, COOH, CCO—($C_1$-$C_6$)-alkyl, CON(R19)(R20), CO(R19), or (CR19R20)$_o$-O(R21);

o and o' are independently 0, 1, 2, and 3;

R1 is a radical selected from the group consisting of

R22, R23, R28, R29, R28a and R29a are independently hydrogen or ($C_1$-$C_6$)-alkyl,
R2 is hydrogen; and
R3 and R4 are independently hydrogen or methyl;
or a tautomeric form or a physiologically tolerated salt thereof.

5. The compound according to claim 4, wherein:
R22, R23, R28, R29, R28a and R29a are independently hydrogen or methyl;
or a tautomeric form or a physiologically tolerated salt thereof.

6. The compound according to claim 1, wherein:
Y is —(C=O)—; and
X is —C(R3)(R4)-; or
X is —(C=O)—; and
Y is —C(R3(R4)-;
R is (CR5R6)$_m$-O(R7), or —$CH_2$-phenyl, wherein the phenyl may be substituted once or twice by F, Cl, Br, $CF_3$, O—($C_1$-$C_6$)-alkyl, ($C_1$-$C_6$)-alkyl, O—($C_2$-$C_4$)-haloalkyl, COOH, CCO—($C_1$-$C_6$)-alkyl, CON(R5)(R6), CO(R5), or (CR5R6)$_m'$—O(R7); or
R and X when X is —C(R3)(R4)-, together with the nitrogen atom to which they are attached form a monocyclic, saturated 6-membered ring system to which a benzene nucleus may be fused, whose individual members of the ring systems may be replaced by one to two atomic groups selected from —CHR11-, —CR11R12-, —(C=R11)-, and =C(R11)-;
m and m' are independently 0, 1, 2, or 3;
R5, R6 and R7 are independently hydrogen or ($C_1$-$C_4$)-alkyl;
R11 and R12 are independently hydrogen or ($C_1$-CO-alkyl;
R1 is ($C_5$-$C_8$)-alkyl, —$CH_2$-phenyl, ($C_1$-$C_2$)-alkylene-heteroaryl, —$CH_2$-cyclohexyl, or cyclohexyl, wherein the heteroaryl is thiophene or benzothiophene, and wherein the phenyl, heteroaryl or cyclohexyl may be substituted once or twice by F, Cl, OH, $CF_3$, $OCF_3$, O—($C_1$-$C_6$)- alkyl, $(C_1-C_6)$-alkyl, $(C_0-C_1)$-alkylene-phenyl, O—phenyl, $(C_0-C_1)$-alkylene-heteroaryl, N(R16)(R17), COOH, COO—$(C_1-C_6)$-alkyl, CON(R16)(R17), CO(R16), or $(CR16R17)_0$-O(R18), wherein the phenyl or heteroaryl may in turn be substituted once or twice by F, Cl, OH, $CF_3$, O—$(C_1-C_6)$-alkyl, $(C_1-C_6)$-alkyl, COOH, COO—$(C_1-C_6)$-alkyl, CON(R19)(R20), CO(R19), or $(CR19R20)_0$-O(R21);

o and o' are 0, 1, 2 or 3; or

R1 is a radical selected from the group consisting of

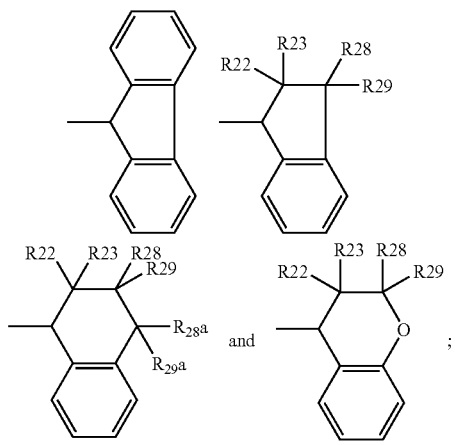

R22, R23, R28, R29, R28a and R29a are independently hydrogen or $(C_1-C_6)$-alkyl;

R2 is hydrogen; and

R3 and R4 are independently hydrogen or methyl;

or a tautomeric form or a physiologically tolerated salt thereof.

7. The compound according to claim 6, wherein:

R22, R23, R28, R29, R28a and R29a are independently hydrogen or methyl;

or a tautomeric form or a physiologically tolerated salt thereof

8. The compound according to claim 1, wherein:

Y is —(C=O)—; and

X is —C(R3)(R4)-; or

X is —(C=O)—; and

Y is —C(R3)(R4)-;

R is HO—$CH_2$—, or benzyl, or

R and X when X is —C(—R3)(R4)-, together form —$CH_2$—$CH_2$—$CH_2$—$CH_2$- or

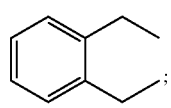

R1 is pentyl, hexyl, heptyl, cyclohexyl, —$CH_2$-cyclohexyl, —$CH_2$-phenyl, —$CH_2$-thiophene, or —$CH_2$—$CH_2$-thiophene, wherein the cyclohexyl, phenyl or thiophene may be substituted by methyl; or R1 is a radical selected from the group consisting of

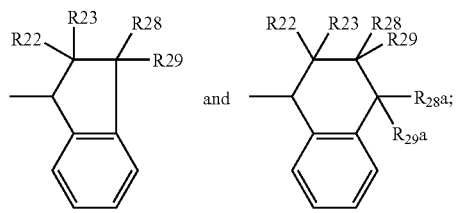

R22, R23, R28, R29, R28a, and R29a are hydrogen;

R2 is hydrogen; and

R3 andR4 are independently hydrogen or methyl;

or a tautomeric form or a physiologically tolerated salt thereof.

9. The compound according to claim 1, which is:

3-Benzyl-2,5-dioxoimidazolidine-1-hexylcarboxamide;

3-Benzyl-2,5-dioxoimidazolidine-1-(2-methylbenzyl)carboxamide;

3-Benzyl-2,5-dioxoimidazolidine-1((S)- indan-1-Acarboxamide;

3-Benzyl-2,5-dioxoimidazolidine-1-((R)-indan-1-yl)carboxamide;

3-Benzyl-2,5-dioxoimidazolidine-1-(1,2,3,4-tetrahydronaphthalen--yl)carboxamide;

3-Benzyl-2,5-dioxoimidazolidine-1-(2-thiophen-2-yl-ethyl)carboxamide;

3-Benzyl-2,5-dioxoimidazolidine-1-heptylcarboxamide;

3-Benzyl-2,4-dioxoimidazolidine-1-hexylcarboxamide;

3-Benzyl-2,4-dioxoimidazolidine-1-(2-methylbenzyl)carboxamide;

3-Benzyl-2,4-dioxoimidazolidine-1-heptylcarboxamide;

3-Benzyl-2,4-dioxoimidazolidine-1-(2-thiophen-2-yl-ethyl)carboxamide;

3-(5,5-Dimethyl-2-oxotetrahydrofuran-3-yl)-5,5-dimethyl-2,4-dioxoimidazolidine-l-hexylcarboxamide;

3-Benzyl-2,5-dioxoimidazolidine-1-pentylcarboxamide;

3-Benzyl-2,5-dioxoimidazolidine-1-cyclohexylcarboxamide;

3-Benzyl-2,5-dioxoimidazolidine-1-cyclohexylmethylcarboxamide;

3-Benzyl-2,5-dioxoimidazolidine-1-benzylcarboxamide;

1,3-Dioxohexahydroimidazo[1,5-a]pyridine-2-hexylcarboxamide;

1,3-Dioxo-1,5,10,10a-tetrahydroimidazo[1,5-]isoquinoline-2-hexylcarboxamide;

1,3-Dioxohexahydroimidazo[1,5-a]pyridine-2-(2-methylbenzyl)carboxamide;

1,3-Dioxo-1,5,10,10a-tetrahydroimidazo[1,5-]isoquinoline-24(S)—indan-1-yl)carboxamide;

1,3-Dioxo-1,5,10,10a-tetrahydroimidazo[1,5-]isoquinoline-24(R)-indan-1-yl)carboxamide;

1,3-Dioxo-1,5,10,10a-tetrahydroimidazo[1,5-]isoquinoline-2-(1,2,3,4-tetrahydronaphthalen-1- y1)carboxamide;

1,3-Dioxo-1,5,10,10a-tetrahydroimidazo[1,5-b ]isoquinoline-2-methylbenzyl-2-carboxamide;

1,3-Dioxohexahydroimidazo[1,5-a]pyridine-24(S)—1,2, 3,4-tetrahydronaphthalen-1- yl)carboxamide;

1,3-Dioxohexahydroimidazo[1,5-a]pyridine-24(S)—indan-1-yl)carboxamide; or 1,3-Dioxohexahydroimidazo[1,5-a]pyridine-24(R)-indan-1-yl)carboxamide;

or a tautomeric form or a physiologically tolerated salt thereof.

10. A pharmaceutical composition comprising the compound according to claim 1, or a tautomeric form or a physiologically tolerated salt thereof, in combination with a pharmacologically acceptable carrier or excipient.

11. A pharmaceutical composition comprising the compound according to claim 9, or a tautomeric form or a physiologically tolerated salt thereof, in combination with a pharmacologically acceptable carrier or excipient.

12. The pharmaceutical composition according to claim 10, further comprising an active ingredient selected from the group consisting of antidiabetics, hypoglycemic active ingredients, FIMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, meglitinides, thiazolidinediones, a-glucosidase inhibitors, active ingredients acting on the ATP-dependent potassium channel of the beta cells, CART agonists, NPY agonists, MC4 agonists, orexin antagonists, H3 agonists, TNF agonists, CRF antagonists, CRF BP antagonists, urocortin agonists, β3 agonists, melanocyte-stimulating hormone agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists, lipase/amylase inhibitors, PPAR modulators, RXR modulators, TR-βagonists and amphetamines.

* * * * *